US010479854B2

(12) United States Patent
Klumperman et al.

(10) Patent No.: US 10,479,854 B2
(45) Date of Patent: Nov. 19, 2019

(54) CONJUGATE FOR TREATING MALARIA

(71) Applicant: Stellenbosch University, Stellenbosch (ZA)

(72) Inventors: Lubertus Klumperman, Leiderdorp (NL); Paul William Reader, Stellenbosch (ZA); Marina Rautenbach, Stellenbosch (ZA)

(73) Assignee: Stellenbosch University, Western Cape Province (ZA)

( * ) Notice: Subject to any disclaimer, the term of this patent is extended or adjusted under 35 U.S.C. 154(b) by 50 days.

(21) Appl. No.: 15/503,175

(22) PCT Filed: Aug. 12, 2015

(86) PCT No.: PCT/IB2015/056148
§ 371 (c)(1),
(2) Date: Feb. 10, 2017

(87) PCT Pub. No.: WO2016/024240
PCT Pub. Date: Feb. 18, 2016

(65) Prior Publication Data

US 2017/0232110 A1 Aug. 17, 2017

(30) Foreign Application Priority Data

Aug. 12, 2014 (ZA) ................................ 2014/05884

(51) Int. Cl.
*A61K 38/08* (2019.01)
*C08F 226/10* (2006.01)

(52) U.S. Cl.
CPC ............ *C08F 226/10* (2013.01); *A61K 38/08* (2013.01); *C08F 2810/40* (2013.01)

(58) Field of Classification Search
None
See application file for complete search history.

(56) References Cited

U.S. PATENT DOCUMENTS

2001/0041172 A1* 11/2001 Bentley ................ A61K 47/482 424/78.19

OTHER PUBLICATIONS

Solovskij et al. (Journal of Controlled Release 58 (1999) 1-8).*
Gumila et al. (Antimicrob Agents Chemother. Mar. 1996;40(3):602-8) (Year: 1996).*
Khanna (International Scholarly Research Network, ISRN Pharmacology, vol. 2012, Article ID 571394, 9 pages) (Year: 2012).*
Eda et al. (Am. J. Trop. Med. Hyg., 71(2), 2004, pp. 190-195) (Year: 2004).*
Urban et al. (Journal of Controlled Release 177 (2014) 84-95) (Year: 2014).*
Romberg et al. (Pharmaceutical Research, vol. 25, No. 1, Jan. 2008) (Year: 2008).*
Leussa Nyango-Nkeh el al: "Characterisation of small cyclic peptides with antilisterial and antimalarial activity", Apr. 1, 2014, Retrieved from the Internet: UEL:http://scholar.sun.ac.za/handle/10019.1/86161.
Luiz A Canalle et al: "Polypeptide-polymer bioconjugates", Chemical Society Reviews, vol. 39, No. 1, Jan. 1, 2010, p. 239.
Petrykina E M et al: "Antimicrobial and hemolytic activity of Gradex", Antibiotiki I Khimioterapiya, vol. 35, No. 8, 1990, pp. 20-22.
Rautenbach et al: "Inhibition of malaria parasite blood stages by tyrocidines, membrane-active cyclic peptide antibiotics from Bacillus brevis", Biochimica et Biophysica Acta (BBA)—Biomembranes, Elsevier, Amsterdam, NL, vol. 1768, No. 6, May 24, 2007, pp. 1488-1497.
Solovski, et al: "Polymer water-soluble derivatives of polypeptide antibiotic, gramicidin-S based on reactive copolymers of N-(2-hydroxypropyl) methacrylamide", Journal of Controlled Release, Elsevier, Amsterdam, vol. 58, Jan. 1, 1999, pp. 1-8.

* cited by examiner

*Primary Examiner* — Sergio Coffa
(74) *Attorney, Agent, or Firm* — Cesari and Mckenna, LLP

(57) ABSTRACT

A peptide-polymer conjugate is provided for use in treating malaria infections, and in particular terminal or drug resistant malaria infections. The conjugate is formed from a polymer to which a peptide having activity against a malaria parasite is co-valently attached. The peptide is a cyclic decapeptide from the closely-related group of tyrocidines, tryptocidines, phenycidines and gramicidin S, and the polymer is a hydrophilic and biocompatible polymer with a terminal thiol, such as poly(N-vinylpyrrolidone) (PVP). The polymer chains can be decorated with a hydrophilic targeting ligand that specifically targets an epitope on red blood cells, and in particular red blood cells infected with a plasmodial parasite. A method for synthesising the peptide-polymer conjugate is also provided.

9 Claims, 16 Drawing Sheets

Specification includes a Sequence Listing.

CONJUGATE FOR TREATING MALARIA

FIELD OF THE INVENTION

The invention provides a peptide-polymer conjugate for use in treating malaria.

CROSS-REFERENCE TO RELATED APPLICATIONS

This application is the National Stage of International Application No. PCT/IB2015/056148, filed on Aug. 12, 2015, which claims priority to South African provisional patent application number 2014/05884. The contents of both applications are hereby incorporated by reference in their entirety.

SEQUENCE LISTING

A computer readable file containing a sequence listing is being electronically co-filed herewith via EFS-Web. The computer readable file, submitted under 37 CFR § 1.821(e), will also serve as the copy required by 37 § CFR 1.821(c). The file (filename "2AG9331.TXT") was created on Feb. 8, 2017 and has a size of 46,217 bytes.

The content of the computer readable file is hereby incorporated by reference in its entirety.

BACKGROUND TO THE INVENTION

Malaria is endemic in 93 third world countries, with an estimated 198 million malaria cases being reported annually (http://www.who.int/malaria/media/world_malaria_report_2014/en/) and resulting in about 367,000-755,000 deaths per year. About 90% of deaths due to malaria occur in Sub-Saharan Africa, and children under the age of 5 years account for more than 70% of these deaths.

Chloroquine and its derivatives and the arternisinins are the main drugs for treating malaria, but global resistance to these drugs is on the increase. For example, chloroquine-resistant strains of *Plasmodium falciparum* (the malaria parasite responsible for most malaria cases) have spread to most malaria areas. There have also been reports of field strains of *P. falciparum* demonstrating in vitro resistance to the artemisinins.

There is therefore an urgent need for an alternative treatment for malaria, especially a last resort antimalarial drug for treating patients (mostly children) with advanced resistant malaria.

Cyclic decapeptides such as the tyrocidines and gramicidin S (i.e. peptides with 10 amino acids forming a ring) are known to have potent antiplasmodial activity. The closely-related tryptocidines and phenycidines, which are cyclic decapeptides with a similar structure, also fall within this group. However, the cyclic decapeptides are considered to be unsuitable for antimalarial treatment as they are haemolytic. Although having a 10-300 fold selectivity towards infected red blood cells, they also lyse healthy red blood cells and other cells, even at micromolar peptide concentrations. They are therefore toxic, especially in a systemic method of treatment.

SUMMARY OF THE INVENTION

According to a first embodiment of the invention, there is provided a peptide-polymer conjugate comprising a polymer to which an antiplasmodial peptide is covalently attached, wherein the peptide is a cyclic decapeptide having an amino acid sequence of cyclo(Val-$X^1$-Leu-D-Phe-Pro-$X^2$-$X^3$-$X^4$-$X^5$-$X^6$) (SEQ ID NO: 1), where:

$X^1$ is Orn or Lys;

$X^2$ is Val, Leu, Ile, Phe, Trp or Tyr;

$X^3$ is the D-isomer of Val, Leu, Ile, Phe, Trp, Tyr or L-isomer of Orn or Lys;

$X^4$ is Asn, Gln or Leu;

$X^5$ is Gln or the D-isomer of Phe; and $X^6$ is Tyr, Phe, Trp, Pro or hydroxyproline (Hyp);

and wherein the peptide-polymer conjugate has activity against a malaria parasite.

The cyclic decapeptide may be a tyrocidine with the sequence cyclo(Val-$X^1$-Leu-D-Phe-Pro-$X^7$-$X^8$-Asn-Gln-$X^9$) (SEQ ID NO: 2) or an analogue or derivative thereof, where:

$X^1$ is Orn or Lys;

$X^7$ is Trp or Phe;

$X^8$ is D-Trp or D-Phe; and $X^9$ is Tyr, Trp or Phe.

Alternatively, the cyclic decapeptide may be gramicidin S or a derivative or analogue thereof, with the amino acid sequence of cyclo(Val-$X^1$-Leu-D-Phe-Pro-Val-$X^1$-Leu-D-Phe-Pro) (SEQ ID NO: 3).

The cyclic decapeptide may be a derivative or analogue of a tyrocidine, tryptocidine, phenycidine or gramicidin S, with one or more of the following amino acid substitutions:

- the valine residue is substituted with a leucine or isoleucine residue;
- the leucine residue is substituted with an isoleucine or valine residue;
- the phenylalanine residue is substituted with a tryptophan or tyrosine residue;
- the proline residue is substituted with a hydroxyproline residue; or
- the ornithine residue is substituted with a lysine or cationic amino acid; or
- an analogue or derivative thereof.

The cyclic decapeptide may have an amino acid sequence selected from any one of SEQ ID NOS: 6-177.

The peptide-polymer conjugate may be produced from a mixture of any two or more peptides of SEQ ID NOS: 6-177.

The polymer may be a water-soluble and biocompatible polymer, and may have a thiol end group. For example, the polymer is selected from the group consisting of poly(N-vinylpyrrolidone), poly(ethylene oxide), poly((ethylene oxide)-co-(propylene oxide)), poly(oligo(ethylene oxide) acrylate), poly(2-hydroxypropyl acrylamide) and poly(oligo (ethylene oxide)methacrylate). In a preferred embodiment, the polymer is poly(N-vinylpyrrolidone).

The peptide may be conjugated to the chain end of the polymer, such as by way of a linkage that is unstable at acidic pH. The linkage is formed via an acrylate ester or via an acrylamide.

The peptide-polymer conjugate may further include a hydrophilic targeting ligand. The targeting ligand may be a peptide which specifically binds to proteins or cell surface markers on the cell surface of red blood cells, and more specifically may be a peptide which specifically binds to proteins or cell surface markers on the cell surface of red blood cells infected with malaria parasites.

The targeting ligand may be selected from peptides having amino acid sequences of SEQ ID NOS: 178-185 and sequences which are at least 50%, at least 60%, at least 70%, at least 80% or at least 90% similar. In one embodiment, the targeting ligand is a peptide having an amino acid sequence which is at least 50% similar to SEQ ID NO: 178, and more particularly is a peptide of SEQ ID NO: 178.

According to a second embodiment of the invention, there is provided a pharmaceutical composition or formulation comprising the peptide-polymer conjugate as described above and a pharmaceutically acceptable carrier.

The peptide-polymer conjugate or pharmaceutical composition or formulation as described above may be for use in treating malaria.

According to a third embodiment of the invention, there is provided the use of a peptide-polymer conjugate as described above in a method of making a medicament for treating malaria.

According to a fourth embodiment of the invention, there is provided a method of treating malaria, the method comprising administering a therapeutically effective amount of a peptide-polymer conjugate or pharmaceutical composition or formulation as described above to a patient in need thereof.

The therapeutically effective amount of the peptide-polymer conjugate may comprise an amount of the peptide which is sub-therapeutic for treating malaria when the peptide is administered in an unconjugated or unmodified form.

According to a fifth embodiment of the invention, there is provided a process for preparing a peptide-polymer conjugate as described above, the process comprising the steps of:

(i) synthesising an acrylate or acrylamide functionalised peptide, wherein the peptide is a cyclic decapeptide having an amino acid sequence of cyclo(Val-$X^1$-Leu-D-Phe-Pro-$X^2$-$X^3$-$X^4$-$X^5$-$X^6$) (SEQ ID NO: 1), where
   $X^1$ is Orn or Lys;
   $X^2$ is Val, Leu, Ile, Phe, Trp or Tyr;
   $X^3$ is the D-isomer of Val, Leu, Ile, Phe, Trp, Tyr or L-isomer of Orn or Lys;
   $X^4$ is Asn, Gln or Leu;
   $X^5$ is Gln or the D-isomer of Phe; and
   $X^6$ is Tyr, Phe, Trp, Pro or hydroxyproline (Hyp), and
(ii) conjugating the acrylate or acrylamide functionalised peptide to the chain end of a water-soluble and biocompatible polymer.

The acrylate or acrylamide functionalised peptide may be conjugated to the polymer by covalently linking an acrylate ester on a tyrosine residue or an acrylamide on a lysine or ornithine residue of the peptide to a terminal thiol on the polymer chain via Michael addition. Preferably, the resulting beta-thioether will cause the ester linkage or the amide linkage to be hydrolytically unstable at acidic pH.

The process may further include the step of conjugating a targeting ligand to the polymer.

The cyclic decapeptide, polymer and targeting ligand may be selected from those described above.

DETAILED DESCRIPTION OF THE INVENTION

Figure 1:
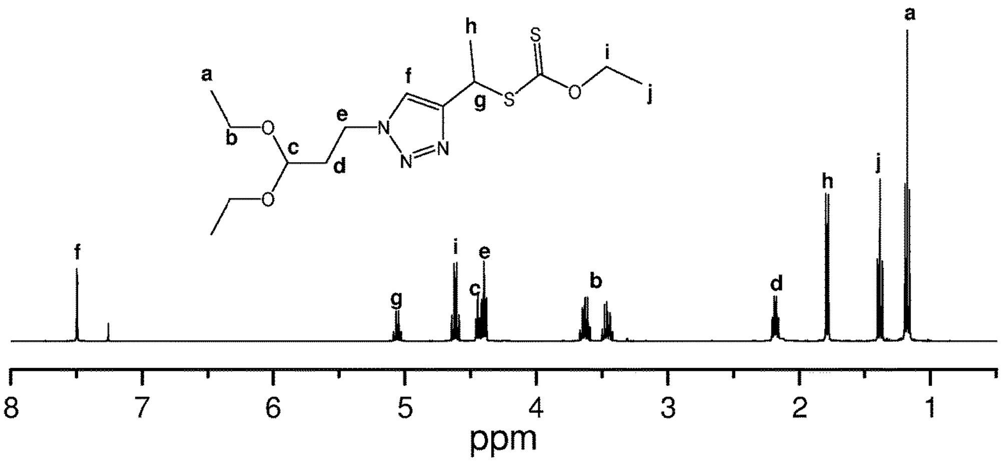
FIG. 1 shows the $^1$H NMR spectrum for RAFT agent 4.

A peptide-polymer conjugate is described herein, wherein the conjugate is formed from a polymer to which an anti-plasmodial peptide is covalently attached. The peptide is a cyclic decapeptide having an amino acid sequence cyclo (Val-$X^1$-Leu-D-Phe-Pro-$X^2$-$X^3$-$X^4$-$X^5$-$X^6$) (SEQ ID NO: 1), where $X^1$ is Orn or Lys;
$X^2$ is Val, Leu, Ile, Phe, Trp or Tyr;
$X^3$ is the D-isomer of Val, Leu, Ile, Phe, Trp, Tyr, or the L-isomer of Orn or Lys;
$X^4$ is Asn, Gln or Leu;
$X^5$ is Gln, or the D-isomer of Phe; and
$X^6$ is Tyr, Phe, Trp, Pro or hydroxyproline (Hyp).

Peptide-polymer conjugates of the invention have anti-plasmodial activity against *Plasmodium falciparum* and analogous parasites (e.g. human malaria parasites including: *P. vivax, P. ovale, P. malariae, P. knowlesi, P. brasilianum; P. cynomolgi, P. cynomolgi bastianellii, P. inui, P. rhodiani, P. schweitzi, P. semiovale* and *P. simium*; primate malaria parasites other than those already listed above including: *P. reichenowi, P. pitheci, P. silvaticum* and *P. fragile*; non-primate malaria parasites including: *P. atheruri; P. berghei; P. bubalis; P. caprae, P. cephalophi; P. cyclopsi; P. odocoilei* and *P. voltaicum*; avian malaria parasites including: *P. relictum, P. anasum, P. hermani, P. gallinaceum, P. cathemerium* and *P. circumflexum*; and others listed at https://en.wikipedia.org/wiki/*Plasmodium*), without the toxicity associated with unconjugated cyclic decapeptides, and are therefore useful for treating malaria in mammals.

Tyrocidines, tryptocidines, phenycidines and/or gramicidin S are β-sheet cyclic decapeptides, with the tyrothricin cyclodecapeptides (the tyrocidines, tryptocidines and phenycidines) being produced by *B. aneurinolyticus* (also known as *Brevibacillus parabrevis*) and gramicidin S being produced by *A. migulanus* (previously known as *B. brevis*). These peptides have high sequence identity, are highly conserved and adopt a similar backbone conformation/molecular topology. Tyrothricin (a tyrocidine/tryptophan/phenycidine-gramicidin complex, where the gramicidins are linear neutral 15-mer peptides not related to gramicidin S) was the first antibiotic to be used in clinical practices, but later fell into disrepute due to its haemolytic toxicity (Dubos and Cattaneo, 1939, J. Exp. Med. 70: 249; Hotchkiss and Dubos, 1941, J. Biol. Chem., 141: 155; Bradshaw, 2003, Biodrugs, 17: 233-240).

Tyrocidines and gramicidin S have a common sequence of Val-Orn-Leu-D-Phe-Pro (SEQ ID NO: 4), where the cationic residue can either be ornithine or lysine. The valine and leucine residues can also be substituted for leucine, isoleucine and valine for tyrocidines. The complete gramicidin S sequence is a repeat of the highly conserved sequence of cyclo(Val-Orn-Leu-D-Phe-Pro)$_2$ (SEQ ID NO: 4). The complete tyrocidine sequence also contains this highly conserved sequence, but instead of a repeat thereof it is followed by a variable pentapeptide moiety, Phe-D-Phe-Asn-Gln-Tyr (SEQ ID NO: 5) or a derivative or analogue thereof. Any one or more of the three aromatic residues in the variable peptide moiety can be substituted with tyrosine, phenylalanine or tryptophan, giving rise to tyrocidines, phenycidines and tryptocidines. There are four tyrocidines (A-D), which may be used in this invention in a purified form or in a mixture of any two or more tyrocidines. Tyrocidine A has the sequence dPhe-Pro-Phe-dPhe-Asn-Gln-Tyr-Val-Orn-Leu; Tyrocidine B has Trp, dPhe and Tyr substitutions at positions 3, 4 and 7, respectively; Tyrocidine C has Trp, dTrp and Tyr substitutions at positions 3, 4 and 7, respectively; and Tyrocidine D has Trp, dTrp and Trp substitutions at positions 3, 4 and 7, respectively. The tyrothricin cyclodecapeptides are produced in a complex mixture, while gramicidin S is produced as a single peptide. In this description, the term "tyrocidine" is intended to refer to any one of tyrocidines A, B, C or D, or a mixture of any two or more thereof.

The primary chemical structures of gramicidin S and tyrocidine A (one of the tyrocidines) are shown below:

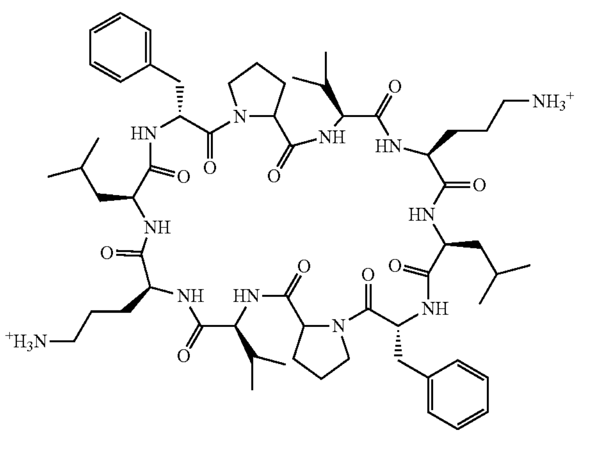

Gramicidin S

-continued

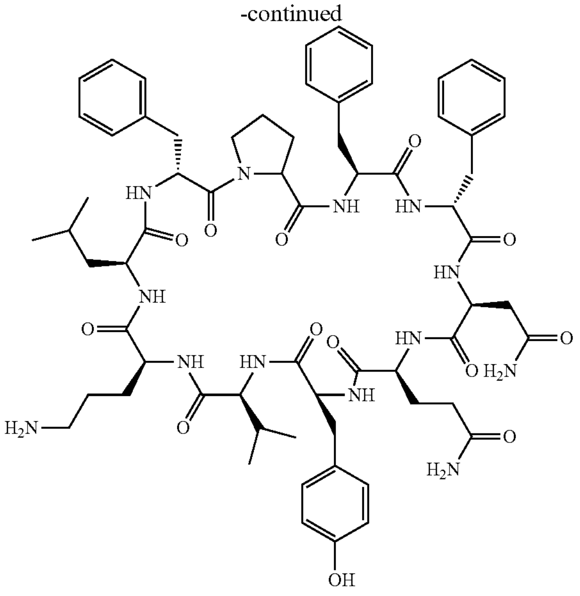

Tyrocidine A

The cyclic decapeptides of the present invention are known tyrocidines, tryptocidines, phenycidines or gramicidin S, or derivatives or analogues thereof, which have a highly conserved amino acid sequence comprising Val-$X^1$-Leu-D-Phe-Pro-$X^2$-$X^3$-$X^4$-$X^5$-$X^6$ (SEQ ID NO: 1), where $X^1$ is ornithine or lysine, or a derivative or analogue thereof.

Suitable analogues of the tyrocidines, tryptocidines, phenycidines or gramicidin S may be those including any one or more of the following substitutions:

- the valine residue substituted with a leucine or isoleucine residue or hydrophobic amino acid or analogue/derivative;
- the leucine residue substituted with an isoleucine or valine residue or hydrophobic amino acid or analogue/derivative;
- the proline residue being replaced by hydroxyproline residue or analogue/derivative thereof;
- the phenylalanine residue substituted with a tryptophan or tyrosine residue or aromatic analogue/derivative thereof;
- the ornithine residue substituted with a lysine or a cationic amino acid or an analogue/derivative thereof;
- $X^2$ being valine, leucine, isoleucine, phenylalanine, tryptophan or tyrosine or a hydrophobic amino acid or analogue/derivative;
- $X^3$ being D-isomer of valine, leucine, isoleucine, phenylalanine, tryptophan or tyrosine or a hydrophobic amino acid or analogue/derivative thereof; or alternatively being an L-isomer of ornithine, lysine or cationic amino acid or analogue/derivative thereof;
- $X^4$ being asparagine, glutamine or leucine or an analogue or derivative thereof;
- $X^5$ being glutamine or a polar amino acid or analogue/derivative thereof; or alternatively being the D-isomer of Phe or a hydrophobic amino acid or analogue/derivative thereof; and
- $X^6$ being a tyrosine, phenylalanine or tryptophan or proline or hydroxyproline residue.

More preferably, the cyclic decapeptide derivatives may be one or more of the peptides selected from the group consisting of:

Tyrocidine Analogues:

(SEQ ID NO: 6)
Cyclo-(VKLfPWwNQY) (Tyrocidine $C_1$, $TrcC_1$)

(SEQ ID NO: 7)
Cyclo-(VOLfPWwNQY) (Tyrocidine C, TrcC)

(SEQ ID NO: 8)
Cyclo-(VKLfPWfNQY) (Tyrocidine $B_1$, $TrcB_1$)

(SEQ ID NO: 9)
Cyclo-(VOLfPWfNQY) (Tyrocidine B, TrcB)

(SEQ ID NO: 10)
Cyclo-(VKLfPFwNQY) (Tyrocidine $B_1$', $TrcB_1$')

(SEQ ID NO: 11)
Cyclo-(VOLfPFwNQY) (Tyrocidine B', TrcB')

(SEQ ID NO: 12)
Cyclo-(VKLfPFfNQY) (Tyrocidine $A_1$, $TrcA_1$)

(SEQ ID NO: 13)
Cyclo-(VOLfPFfNQY) (Tyrocidine A, TrcA)

(SEQ ID NO: 14)
Cyclo-(VKLfPYwNQY)

(SEQ ID NO: 15)
Cyclo-(VOLfPYwNQY)

(SEQ ID NO: 16)
Cyclo-(VKLfPYfNQY)

(SEQ ID NO: 17)
Cyclo-(VOLfPYfNQY)

(SEQ ID NO: 18)
Cyclo-(VKLfPFyNQY)

(SEQ ID NO: 19)
Cyclo-(VOLfPFyNQY)

(SEQ ID NO: 20)
Cyclo-(VKLfPWyNQY)

(SEQ ID NO: 21)
Cyclo-(VOLfPWyNQY)

(SEQ ID NO: 22)
Cyclo-(LKLfPWwNQY)

(SEQ ID NO: 23)
Cyclo-(LOLfPWwNQY)

(SEQ ID NO: 24)
Cyclo-(LKLfPWfNQY)

(SEQ ID NO: 25)
Cyclo-(LOLfPWfNQY)

(SEQ ID NO: 26)
Cyclo-(LKLfPFwNQY)

(SEQ ID NO: 27)
Cyclo-(LOLfPFwNQY)

(SEQ ID NO: 28)
Cyclo-(LKLfPFfNQY)

(SEQ ID NO: 29)
Cyclo-(LOLfPFfNQY)

(SEQ ID NO: 30)
Cyclo-(LKLfPYwNQY)

(SEQ ID NO: 31)
Cyclo-(LOLfPYwNQY)

-continued (SEQ ID NO: 32)
Cyclo-(LKLfPYfNQY)

(SEQ ID NO: 33)
Cyclo-(LOLfPYfNQY)

(SEQ ID NO: 34)
Cyclo-(LKLfPFyNQY)

(SEQ ID NO: 35)
Cyclo-(LOLfPFyNQY)

(SEQ ID NO: 36)
Cyclo-(LKLfPWyNQY)

(SEQ ID NO: 37)
Cyclo-(LOLfPWyNQY)

(SEQ ID NO: 38)
Cyclo-(IKLfPWwNQY)

(SEQ ID NO: 39)
Cyclo-(IOLfPWwNQY)

(SEQ ID NO: 40)
Cyclo-(IKLfPWfNQY)

(SEQ ID NO: 41)
Cyclo-(IOLfPWfNQY)

(SEQ ID NO: 42)
Cyclo-(IKLfPFwNQY)

(SEQ ID NO: 43)
Cyclo-(IOLfPFwNQY)

(SEQ ID NO: 44)
Cyclo-(IKLfPFfNQY)

(SEQ ID NO: 45)
Cyclo-(IOLfPFfNQY)

(SEQ ID NO: 46)
Cyclo-(IKLfPYwNQY)

(SEQ ID NO: 47)
Cyclo-(IOLfPYwNQY)

(SEQ ID NO: 48)
Cyclo-(IKLfPYfNQY)

(SEQ ID NO: 49)
Cyclo-(IOLfPYfNQY)

(SEQ ID NO: 50)
Cyclo-(IKLfPFyNQY)

(SEQ ID NO: 51)
Cyclo-(IOLfPFyNQY)

(SEQ ID NO: 52)
Cyclo-(IKLfPWyNQY)

(SEQ ID NO: 53)
Cyclo-(IOLfPWyNQY)

(SEQ ID NO: 54)
Cyclo-(VKLfPLwNQY)

(SEQ ID NO: 55)
Cyclo-(VOLfPLwNQY)

(SEQ ID NO: 56)
Cyclo-(VKLfPLfNQY)

(SEQ ID NO: 57)
Cyclo-(VOLfPLfNQY)

-continued

Cyclo-(VKLfPLyNQY) (SEQ ID NO: 58)

Cyclo-(VOLfPLyNQY) (SEQ ID NO: 59)

Tryptocidine Analogues:

Cyclo-(VKLfPWwNQW) (Tryptocidine $C_1$, $TpcC_1$) (SEQ ID NO: 60)

Cyclo-(VOLfPWwNQW) (Tryptocidine C, TpcC) (SEQ ID NO: 61)

Cyclo-(VKLfPWfNQW) (Tryptocidine $B_1$, $TpcB_1$) (SEQ ID NO: 62)

Cyclo-(VOLfPWfNQW) (Tryptocidine B, TpcB) (SEQ ID NO: 63)

Cyclo-(VKLfPFwNQW) (Tryptocidine $B_1$', $TpcB_1$') (SEQ ID NO: 64)

Cyclo-(VOLfPFwNQW) (Tryptocidine B', TpcB') (SEQ ID NO: 65)

Cyclo-(VKLfPFfNQW) (Tryptocidine $A_1$, $TpcA_1$) (SEQ ID NO: 66)

Cyclo-(VOLfPFfNQW) (Tryptocidine A, TpcA) (SEQ ID NO: 67)

Cyclo-(VKLfPYwNQW) (SEQ ID NO: 68)

Cyclo-(VOLfPYwNQW) (SEQ ID NO: 69)

Cyclo-(VKLfPYfNQW) (SEQ ID NO: 70)

Cyclo-(VOLfPYfNQW) (SEQ ID NO: 71)

Cyclo-(VKLfPFyNQW) (SEQ ID NO: 72)

Cyclo-(VOLfPFyNQW) (SEQ ID NO: 73)

Cyclo-(VKLfPWyNQW) (SEQ ID NO: 74)

Cyclo-(VOLfPWyNQW) (SEQ ID NO: 75)

Cyclo-(LKLfPWwNQW) (SEQ ID NO: 76)

Cyclo-(LOLfPWwNQW) (SEQ ID NO: 77)

Cyclo-(LKLfPWfNQW) (SEQ ID NO: 78)

Cyclo-(LOLfPWfNQW) (SEQ ID NO: 79)

Cyclo-(LKLfPFwNQW) (SEQ ID NO: 80)

Cyclo-(LOLfPFwNQW) (SEQ ID NO: 81)

Cyclo-(LKLfPFfNQW) (SEQ ID NO: 82)

Cyclo-(LOLfPFfNQW) (SEQ ID NO: 83)

-continued

Cyclo-(LKLfPYwNQW) (SEQ ID NO: 84)

Cyclo-(LOLfPYwNQW) (SEQ ID NO: 85)

Cyclo-(LKLfPYfNQW) (SEQ ID NO: 86)

Cyclo-(LOLfPYfNQW) (SEQ ID NO: 87)

Cyclo-(LKLfPFyNQW) (SEQ ID NO: 88)

Cyclo-(LOLfPFyNQW) (SEQ ID NO: 89)

Cyclo-(LKLfPWyNQW) (SEQ ID NO: 90)

Cyclo-(LOLfPWyNQW) (SEQ ID NO: 91)

Cyclo-(IKLfPWwNQW) (SEQ ID NO: 92)

Cyclo-(IOLfPWwNQW) (SEQ ID NO: 93)

Cyclo-(IKLfP(Wf)NQW) (SEQ ID NO: 94)

Cyclo-(IOLfP(Wf)NQW) (SEQ ID NO: 95)

Cyclo-(IKLfP(Fw)NQW) (SEQ ID NO: 96)

Cyclo-(IOLfP(Fw)NQW) (SEQ ID NO: 97)

Cyclo-(IKLfPFfNQW) (SEQ ID NO: 98)

Cyclo-(IOLfPFfNQW) (SEQ ID NO: 99)

Cyclo-(IKLfPYwNQW) (SEQ ID NO: 100)

Cyclo-(IOLfPYwNQW) (SEQ ID NO: 101)

Cyclo-(IKLfPYfNQW) (SEQ ID NO: 102)

Cyclo-(IOLfPYfNQW) (SEQ ID NO: 103)

Cyclo-(IKLfPFyNQW) (SEQ ID NO: 104)

Cyclo-(IOLfPFyNQW) (SEQ ID NO: 105)

Cyclo-(IKLfPWyNQW) (SEQ ID NO: 106)

Cyclo-(IOLfPWyNQW) (SEQ ID NO: 107)

Cyclo-(VKLfPLwNQW) (SEQ ID NO: 108)

Cyclo-(VOLfPLwNQW) (SEQ ID NO: 109)

Cyclo-(VKLfPLfNQW) (SEQ ID NO: 110)

-continued (SEQ ID NO: 111)
Cyclo-(VOLfPLfNQW)

(SEQ ID NO: 112)
Cyclo-(VKLfPLyNQW)

(SEQ ID NO: 113)
Cyclo-(VOLfPLyNQW)

Phenycidine Analogues:

(SEQ ID NO: 114)
Cyclo-(VKLfPWwNQF) (Phenycidine $C_1$, $PhcC_1$)

(SEQ ID NO: 115)
Cyclo-(VOLfPWwNQF) (Phenycidine C, PhcC)

(SEQ ID NO: 116)
Cyclo-(VKLfPWfNQF) (Phenycidine $B_1$, $PhcB_1$)

(SEQ ID NO: 117)
Cyclo-(VOLfPWfNQF) (Phenycidine B, PhcB)

(SEQ ID NO: 118)
Cyclo-(VKLfPFwNQF) (Phenycidine $B_1$', $PhcB_1$')

(SEQ ID NO: 119)
Cyclo-(VOLfPFwNQF) (Phenycidine B', PhcB')

(SEQ ID NO: 120)
Cyclo-(VKLfPFfNQF) (Phenycidine $A_1$, $PhcA_1$)

(SEQ ID NO: 121)
Cyclo-(VOLfPFfNQF) (Phenycidine A or Tyrocidine E, PhcA)

(SEQ ID NO: 122)
Cyclo-(VKLfPYwNQF)

(SEQ ID NO: 123)
Cyclo-(VOLfPYwNQF)

(SEQ ID NO: 124)
Cyclo-(VKLfPYfNQF)

(SEQ ID NO: 125)
Cyclo-(VOLfPYfNQF)

(SEQ ID NO: 126)
Cyclo-(VKLfPFyNQF)

(SEQ ID NO: 127)
Cyclo-(VOLfPFyNQF)

(SEQ ID NO: 128)
Cyclo-(VKLfPWyNQF)

(SEQ ID NO: 129)
Cyclo-(VOLfPWyNQF)

(SEQ ID NO: 130)
Cyclo-(LKLfPWwNQF)

(SEQ ID NO: 131)
Cyclo-(LOLfPWwNQF)

(SEQ ID NO: 132)
Cyclo-(LKLfPWfNQF)

(SEQ ID NO: 133)
Cyclo-(LOLfPWfNQF)

(SEQ ID NO: 134)
Cyclo-(LKLfPFwNQF)

(SEQ ID NO: 135)
Cyclo-(LOLfPFwNQF)

-continued (SEQ ID NO: 136)
Cyclo-(LKLfPYwNQF)

(SEQ ID NO: 137)
Cyclo-(LOLfPYwNQF)

(SEQ ID NO: 138)
Cyclo-(LKLfPYfNQF)

(SEQ ID NO: 139)
Cyclo-(LOLfPYfNQF)

(SEQ ID NO: 140)
Cyclo-(LKLfPFyNQF)

(SEQ ID NO: 141)
Cyclo-(LOLfPFyNQF)

(SEQ ID NO: 142)
Cyclo-(LKLfPWyNQF)

(SEQ ID NO: 143)
Cyclo-(LOLfPWyNQF)

(SEQ ID NO: 144)
Cyclo-(LKLfPFfNQF)

(SEQ ID NO: 145)
Cyclo-(LOLfPFfNQF)

(SEQ ID NO: 146)
Cyclo-(IKLfPWwNQF)

(SEQ ID NO: 147)
Cyclo-(IOLfPWwNQF)

(SEQ ID NO: 148)
Cyclo-(IKLfPWfNQF)

(SEQ ID NO: 149)
Cyclo-(IOLfPWfNQF)

(SEQ ID NO: 150)
Cyclo-(IKLfPFwNQF)

(SEQ ID NO: 151)
Cyclo-(IOLfPFwNQF)

(SEQ ID NO: 152)
Cyclo-(IKLfPYwNQF)

(SEQ ID NO: 153)
Cyclo-(IOLfPYwNQF)

(SEQ ID NO: 154)
Cyclo-(IKLfPYfNQF)

(SEQ ID NO: 155)
Cyclo-(IOLfPYfNQF)

(SEQ ID NO: 156)
Cyclo-(IKLfPFyNQF)

(SEQ ID NO: 157)
Cyclo-(IOLfPFyNQF)

(SEQ ID NO: 158)
Cyclo-(IKLfPWyNQF)

(SEQ ID NO: 159)
Cyclo-(IOLfPWyNQF)

(SEQ ID NO: 160)
Cyclo-(IKLfPFfNQF)

(SEQ ID NO: 161)
Cyclo-(IOLfPFfNQF)

(SEQ ID NO: 162)
Cyclo-(VKLfPLwNQF)

-continued (SEQ ID NO: 163)
Cyclo-(VOLfPLwNQF)

(SEQ ID NO: 164)
Cyclo-(VKLfPLfNQF)

(SEQ ID NO: 165)
Cyclo-(VOLfPLfNQF)

(SEQ ID NO: 166)
Cyclo-(VKLfPLyNQF)

(SEQ ID NO: 167)
Cyclo-(VOLfPLyNQF)

Gramicidin S Analogues:

(SEQ ID NO: 168)
Cyclo-(VOLfPVOLfP) (Gramicidin S)

(SEQ ID NO: 169)
Cyclo-(VKLfPVOLfP)

(SEQ ID NO: 170)
Cyclo-(VKLfPVKLfP)

(SEQ ID NO: 171)
Cyclo-(LOLfPVOLfP)

(SEQ ID NO: 172)
Cyclo-(LKLfPVOLfP)

(SEQ ID NO: 173)
Cyclo-(LOLfPVKLfP)

(SEQ ID NO: 174)
Cyclo-(LKLfPVKLfP)

(SEQ ID NO: 175)
Cyclo-(LOLfPLOLfP)

(SEQ ID NO: 176)
Cyclo-(LKLfPLOLfP)

(SEQ ID NO: 177)
Cyclo-(LKLfPLKLfP)

In the sequences above, standard upper case abbreviations denote L-amino acids (with the exception of O for ornithine), lower case abbreviations denote a D-residue and cyclo indicates amino to carboxy-terminal cyclisation via an amide bond.

References herein to "cyclic decapeptides" refer to the sequences stated above and analogues or derivatives thereof.

The cyclic decapeptides can be produced by their natural bacterial producers, by genetically modifying a suitable microorganism or by using an organic/semi-synthetic system. The amino acid residues in the derivatives or analogues can separately or in combination be replaced in the core cyclic decapeptide sequence (cyclo(Val-Orn-Leu-D-Phe-Pro-$X^2$-$X^3$-$X^4$-$X^5$-$X^6$) (SEQ ID NO: 1) by bacterial/microbial production or using organic/semi-synthetic systems.

In the present invention, the cyclic decapeptide can be covalently attached to the chain end of a polymer, which is preferably a hydrophilic and biocompatible polymer with a terminal thiol (although a person skilled in the art will understand that chemical linkers may alternatively be used if the polymer does not have a thiol end group). The covalent link can be formed by an acrylate ester on the tyrosine residue of a tyrocidine or by an acrylamide on the lysine or ornithine residue on tryptocidines/phenycidines/tyrocidines and gramicidin S, and by subsequent linking via Michael addition to a terminal thiol on the polymer chain. The beta-thioether causes the ester linkage or the amide linkage to be hydrolytically unstable at acidic pH.[12] The peptides may be modified to have more than one acrylate ester or acrylamide.

For example, the acrylate can be introduced onto the tyrosine residue of tyrocidine with an acid chloride derivative of acrylate (e.g. acryloyl chloride) or an activated ester of acrylic acid via ester formation, using DMF or DMSO as a solvent and an organic base such as triethylamine or diisopropylethylamine (DIPEA) as a catalyst. The temperature of this reaction should be kept below 40° C. to avoid polymerisation of the acrylate, and more particularly should be kept at about 0° C. to prevent side reactions. The thiol-Michael reaction is a "click" reaction which can be performed under "green" conditions. In one method of carrying out this reaction, the polymer and cyclic decapeptides with an acrylate derivative or acrylamide derivative are reacted in a solvent such as water or water/DMF and a catalyst such as a nucleophilic phosphine (e.g. Tris(2-carboxyethyl)phosphine (TCEP) or tributyl phosphine) or an amine (e.g. triethylamine, hexylamine or ethylenediamine). The reaction can be performed at ambient temperature or a temperature in the range of from about 20° C. to about 40° C.

Suitable polymers include poly(N-vinylpyrrolidone), poly (ethylene oxide), poly((ethylene oxide)-co-(propylene oxide)), poly(oligo(ethylene oxide)acrylate), poly(oligo(ethylene oxide)methacrylate), poly(2-hydroxypropyl acrylamide) or any other suitably reactive water-soluble polymer. In one preferred embodiment, the polymer is poly(N-vinylpyrrolidone) (PVP).

The polymer preferably has a number average molecular weight between 1,000 and 20,000 g/mol, more preferably between 1,000 and 10,000 g/mol and most preferably between 1,000 and 6,000 g/mol.

The polymer chains can optionally be decorated with a peptide sequence that specifically targets an epitope on red blood cells, which may be only those red blood cells infected with a plasmodial parasite or normal red blood cells too (typically, about 1% of the polymer chains will be decorated with these targeting ligands). The targeting peptide (also referred to herein as the targeting ligand) is typically hydrophilic.

Figure 4:
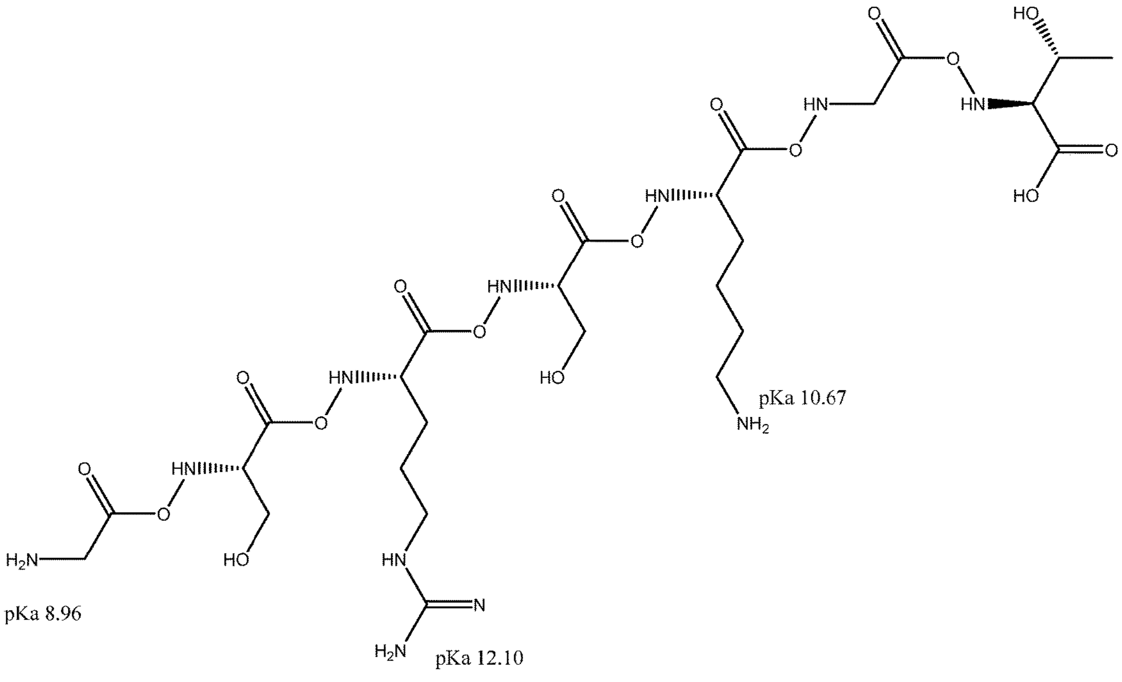
FIG. 4 shows targeting ligand Gly-Ser-Arg-Ser-Lys-Gly-Thr (SEQ ID NO: 178)

Examples of suitable targeting ligands include, but are not limited to, the peptides which Eda et al.[6] have previously described as targeting proteins displayed on the cell surface of malaria parasite-infected red blood cells (Gly-Ser-Arg-Ser-Lys-Gly-Thr (SEQ ID NO: 178), Leu-Val-Asp-Ala-Ala-Ala-Leu (SEQ ID NO: 179), Pro-Ile-Ala-Leu-Gly-Leu-Lys (SEQ ID NO: 180), Gly-Gly-Pro-Leu-Lys-Gly-Leu (SEQ ID NO: 181), Ile-Asn-Leu-Gly-Leu-Thr-Met (SEQ ID NO: 182), Phe-Ser-Leu-Gly-Leu-Ile-Lys (SEQ ID NO: 183), Pro-Ala-Tyr-Lys-Leu-Tyr-Ser (SEQ ID NO: 184) or Asn-Ser-Val-Gly-Gly-Arg-Ser (SEQ ID NO: 185)), or peptides which have amino acid sequences which are at least 50%, at least 60%, at least 70%, at least 80%, or at least 90% similar thereto. In one embodiment, the targeting ligand has the amino acid sequence Gly-Ser-Arg-Ser-Lys-Gly-Thr (SEQ ID NO: 178) (FIG. 4). This peptide was selected for proof of concept studies because of its overt hydrophilicity. It has four amine groups that can react with an aldehyde, and it was selectively conjugated by manipulating the pH of the reaction buffer to keep the N-terminus neutral, thereby promoting the N-terminal coupling reaction, while the Lys and Arg residues remained positively charged. Alternatively, coupling can be via a carboxyl group on the polymer with selective activation and coupling by utilising, for example, N-ethyl-N'-(3-dimethylaminopropyl)carbodiimide as carboxyl activation agent.

Due to the self-assembling nature of the more hydrophobic cyclic decapeptide and the hydrophilic nature of the polymer and targeting ligand, the conjugate is amphiphilic and self-assembles into micelles (measurements show that they are around 20 nm in diameter (FIG. 10)), with the targeting ligands being decorated on the surfaces of the micelles.

The micelles are efficiently taken up in red blood cells, with the peptide-polymer conjugate acting as a "Trojan-horse" drug carrier. In the case of parasite-infected erythrocytes, the micelles are subsequently taken up by the parasite and end up in their food vacuole where the pH is below 6 (about pH5.5). This is sufficient for the hydrolytically unstable ester or amide to be cleaved and for the cyclic decapeptide to be liberated inside the cell. After cleavage of the conjugate, the peptide reverts to its original form and is able to lyse the malarial/plasmodial parasite within the red blood cell. The polymer is excreted from the cell and body of the mammal.

Two versions of the conjugate of the invention were synthesized, using tyrocidine as the cyclic decapeptide and poly(N-vinylpyrrolidone) (PVP) of two different lengths as the polymer. These were tested in an anti-malaria assay (Malstat assay) and an haemolytic assay, and it was found that the concentration of a tyrocidine/tryptocidine mixture required to kill malaria in infected red blood cells dropped by a factor of close to 500 (it was reduced to the μg/mL range) when delivered via the conjugate compared to the administration of free tyrocidine. More importantly, at a concentration where all the malaria infected cells were killed within 24 hours, healthy red blood cells were unaffected.

Thus, the peptide-polymer conjugate of the invention was shown to be close to 500 times more potent than the tyrocidine/tryptocidine mixture on its own and is highly selective at therapeutically relevant concentrations. The therapeutically active drug loading is also exceptionally low (below 50 ng/mL), which could also have cost benefits or reduce potential side effects of the peptide-polymer conjugate or the cyclic decapeptides.

As the malaria assay was performed on a chloroquine-resistant malaria strain, the peptide-polymer conjugate could also be useful in treating drug-resistant malaria strains.

The invention will now be described in more detail with reference to the following non-limiting examples:

EXAMPLES

Material and Methods

All chemicals and solvents were purchased from commercial sources and used without further purification, unless stated otherwise. 2,2'-azobis(isobutyronitrile) (AIBN) (Riedel-de Haën) was recrystallized from methanol and dried under vacuum at ambient temperature. All solvents and monomers were dried and distilled before use. Reactions were monitored using thin layer chromatography (TLC), utilising Machery-Nagel Silica gel 60 plates with a UV 254 fluorescent indicator. Dialysis tubing, MWCO 2000, was purchased from Sigma Aldrich. Moisture and oxygen sensitive reactions were carried out in an inert argon atmosphere. $^{1}$H-NMR and $^{13}$C-NMR spectra were recorded on a Varian VXR-Unity (400 MHz) spectrometer. Samples were prepared in deuterated solvents obtained from Cambridge Isotope labs. Chemicals shifts were reported in parts-per-million (ppm), referenced to the residual solvent protons. Size exclusion chromatography (SEC) was measured on a system that comprised a Shimadzu LC-10AT isocratic pump, a Waters 717+autosampler, a column system fitted with a PSS guard column (50×8 mm) in series with three PSS GRAM columns (300×8 mm, 10 μm, 2×3000 Å and 100 Å) kept at 40° C., a Waters 2487 dual wavelength UV detector and a Waters 2414 differential refractive index (DRI) detector. Dimethylacetamide (DMAc) was used as the eluent, stabilized with 0.05% BHT (w/v) and 0.03% LiCl (w/v), at a flow rate of 1 mL·min$^{-1}$. The polymer samples were filtered through 0.45 μm GHP filters, to remove impurities, prior to analysis. Calibration was carried out using poly(methyl methacrylate) (PMMA) standard sets (Polymer Laboratories) ranging from 690 to 1.2×10$^{6}$ g/mol. Data acquisition was performed using Millennium[32] software, version 4.

Fluorescence spectroscopy was performed on a Carl Zeiss Confocal LSM 780 Elyra S1, equipped with a LSM780 GaAsP detector, using an alpha Plan-Apochromat 100×/1.46 oil DIC objective. Samples were excited with a 488 nm laser with utilisation of a MBS 488/561 beam splitter. Images were acquired through z-stacking with an increment of 0.3 μm step width, and projected as maximum intensity projections using ZEN software (black edition, 2011).

Ultra performance liquid chromatography coupled to electrospray mass spectroscopy (UPLC-MS) was measured on a system that comprised a Waters Acquity Ultra Performance Liquid Chromatograph coupled to a Waters Q-Tof Ultima mass spectrometer fitted with a Z-spray electrospray ionisation source. The system was tailored with a Waters UPLC BEH $C_{18}$ column (2.1×50 mm, 1.7 μm spherical particles, Millipore-Waters, La Jolla, USA). For direct injections and ESMS analysis, 3 μL of the sample solution (±50 ng peptide in 50% MeCN) were injected each time. For UPLC, 1-3 μL of the sample solution (±50 ng peptide in 50% MeCN) was injected each time. Separation was achieved using a 0.1% trifluoroacetic acid (A) to MeCN (B) gradient (100% A for 30 seconds, 0 to 30% B from 30 to 60 seconds, 30 to 60% B from 1 to 10 minutes, 60 to 80% B from 10 to 15 minutes at a flow rate of 300 μL/min), followed by re-equilibration of the column to initial conditions.

Transmission electron microscopy (TEM) was performed on a FEI Tecnai G2 20 TWIN with a Gatan Tridiem 863 energy filter, incorporating a built-in CCD camera microscope, operating with an accelerating voltage of 120 kV. The samples were prepared on a plasma-treated copper grid.

Light microscopy was performed on a Nikon Eclipse E600 fluorescence microscope fitted with a 100×Apochromat objective and images were captured with a Media Cybernetics CoolSNAP-Pro monochrome cooled CCD camera. Confocal fluorescence microscopy (CFM) was performed on a Carl Zeiss LSM 780. The images were taken using a 488 nm (100 mW) laser (green).

Human umbilical vein endothelial cells (HUVECs) passaged less than 6 times were used in the assessment of the toxicity of the conjugate. HUVECs (cc-2159; Lonza, Walkersville, Md.) were cultured in collagen-coated flasks using EBM™ Basal Medium with supplements added (cc-3121 & cc-4133; Lonza, Walkersville, Md.) and maintained in a humidified atmosphere at 37° C. in the presence of 5% $CO_2$.

1. Synthesis of polyvinylpyrrolidone (PVP)

Polyvinylpyrrolidone (PVP) was synthesised by a RAFT polymerisation process. Akeroyd et al. showed that a 1,2,3 triazole-based RAFT agent offered good control over molar mass and dispersity for vinyl acetate, styrene, n-butyl acrylate and N-vinylpyrrolidone (NVP). It also allowed the introduction of a vast range of functionalities through copper click chemistry (scheme 1).[1]

Scheme 1 - Triazole-based RAFT agent

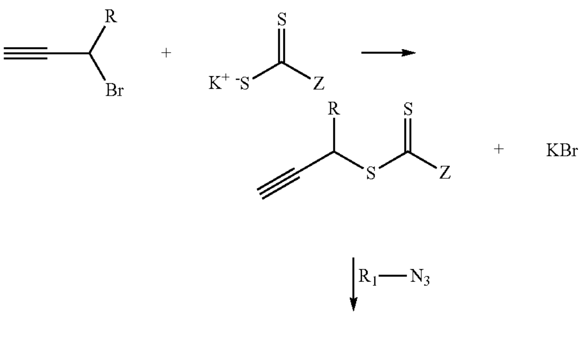

-continued

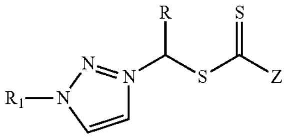

where R = H, $CH_3$

A new RAFT agent (4) was designed in line with this strategy (Scheme 2). It contained both a xanthate and an acetal functionality.

Scheme 2 - Synthesis of RAFT agent 4

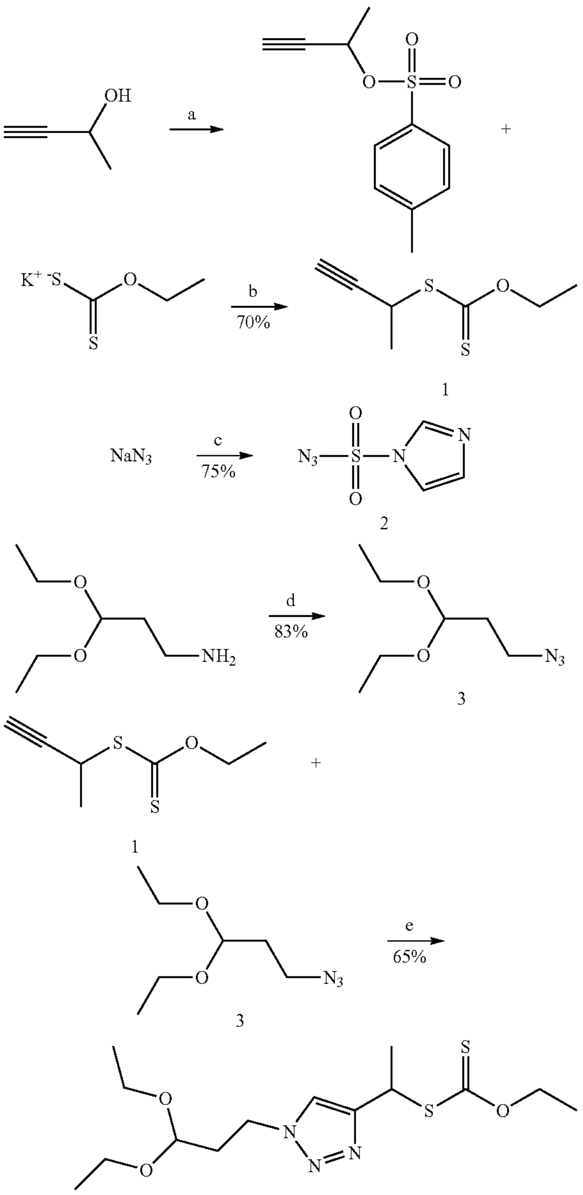

(a) Tosyl chloride (TsCl), KOH, 0° C.; (b) Room temperature (r.t.); (c) $SO_2Cl_2$, 0° C. to r.t.; imidazole (d) 2, $K_2CO_3$, $CuSO_4{\bullet}H_2O$, Sodium ascorbate, r.t.; (e) $CuSO_4{\bullet}H_2O$, Sodium ascorbate, r.t.

Synthesis of O-(but-3-yn-2-yl)O-ethyl carbonothioate (1)

But-3-yn-2-ol (10.0 g, 142 mmol), tosyl chloride (32.6 g, 171 mmol) and diethyl ether (100 mL) were introduced into a 250 mL round bottom flask and the mixture was cooled to 0° C. in a sodium chloride/ice bath. Potassium hydroxide (20.2 g, 360 mmol) was slowly added portion-wise over 20 minutes after which the suspension was stirred for 3 hours, warming to room temperature on its own accord. After that, the reaction mixture was filtered, washed with water (2×50 mL), dried over magnesium sulphate and concentrated, yielding the crude white crystalline product, which was used immediately in the next step. Potassium ethyl xanthate (20.6 g, 129 mmol) and THF (80 mL) were added to the crude activated alcohol (24.0 g, 107 mmol) in a 250 mL round bottom flask and allowed to run at room temperature overnight. The reaction mixture was filtered, concentrated and then purified via column chromatography (diethyl ether: pentane=8:2) to yield 1 as a pale yellow oil (16.41 g, 66% overall). $^1H$ NMR (400 MHz, $CDCl_3$) δ 4.66 (q, J=7.1 Hz, 2H), 4.47 (qd, J=7.1, 2.5 Hz, 1H), 2.33 (d, J=2.5 Hz, 1H), 1.62 (d, J=7.1 Hz, 3H), 1.43 (t, J=7.1 Hz, 3H). $^{13}C$ NMR (400 MHz, $CDCl_3$) δ 212.33, 83.08, 71.67, 70.33, 35.24, 21.42, 13.96.

Synthesis of imidazole-1-sulfonyl azide hydrochloride (2)

This compound was prepared as described in Goddard-Borger and Stick (2007).[2] 1H NMR (400 MHz, D2O) δ 9.33 (t, J=1.3 Hz, 1H), 8.04-8.00 (m, 1H), 7.60 (dd, J=2.1, 1.2 Hz, 1H).

Synthesis of 3-azido-1,1-diethoxypropane (3)

The synthesis of 3 was adapted from literature.[2] 1-Amino-3,3-diethoxypropane (5.00 g, 34.0 mmol), potassium carbonate (9.39 g, 68.0 mmol), copper (II) sulphate.$5H_2O$ (84.9 mg, 0.340 mmol) and MeOH (30 mL) were introduced into a 100 mL round bottom flask. 2 (8.50 g, 40.1 mmol) was dissolved in MeOH (20 mL) and added to the reaction mixture and the solution was stirred for 10 hours at room temperature. The mixture was diluted with water (30 mL), acidified to pH 6 using acetic acid and extracted into diethyl ether (4×50 mL). The combined organic layers were washed with water (2×50 mL) and brine (2×50 mL), dried over magnesium sulphate and concentrated affording a dark yellow oil 3 (4.52 g, 77%). $^1H$ NMR (400 MHz, $CDCl_3$) δ 4.59 (t, J=5.6 Hz, 1H), 3.74-3.58 (m, 2H), 3.55-3.45 (m, 2H), 3.36 (t, J=6.8 Hz, 2H), 1.87 (td, J=6.8, 5.7 Hz, 2H), 1.20 (t, J=7.1 Hz, 6H). $^{13}C$ NMR (400 MHz, $CDCl_3$) δ 103.56, 64.00, 49.85, 32.91, 15.45.

Synthesis of O-(1-(1-(3,3-diethoxypropyl)-1H-1,2,3-triazol-4-yl)ethyl)O-ethyl Carbonothioate (4)

A 50 mL round bottom flask was charged with 1 (3.71 g, 21.4 mmol), 3 (3.71 g, 21.4 mmol), copper (II) sulphate.$5H_2O$ (0.53 g, 2.14 mmol), sodium ascorbate (1.27 g, 6.43 mmol), DMF (15 mL) and stirred overnight at room temperature. The product was concentrated and purified via column chromatography (diethyl ether:pentane=4:1) to afford a viscous yellow oil 4 (4.46 g, 60%). $^1H$ NMR (400 MHz, $CDCl_3$) δ 7.50 (s, 1H), 5.06 (q, J=7.2 Hz, 1H), 4.62 (q, J=7.1 Hz, 2H), 4.45 (t, J=5.4 Hz, 1H), 4.40 (t, J=7.1 Hz, 2H), 3.63 (dq, J=9.3, 7.1 Hz, 2H), 3.53-3.40 (m, 2H), 2.18 (td, J=7.0, 5.5 Hz, 2H), 1.79 (d, J=7.2 Hz, 3H), 1.38 (t, J=7.1 Hz, 3H), 1.18 (t, J=7.0 Hz, 6H). $^{13}C$ NMR (400 MHz, $CDCl_3$) δ 213.34, 148.28, 121.79, 100.48, 70.11, 62.40, 46.44, 41.02, 34.54, 20.44, 15.49, 13.97. MS (ESI): m/z=348.1 (calculated 348.1 for $[M+H^+]$).

$^1H$ NMR confirmed that the RAFT agent 4 contained no impurities (FIG. 1). It also showed the characteristic triazole proton (f) at 7.5 ppm.

NVP was polymerised using RAFT agent 4. NVP (10.0 g, 90.0 mmol), AIBN (37.0 mg, 0.225 mmol), 4 (0.312 g, 0.900 mmol) and anisole (10 mL) were added to a 30 mL pear flask. The reaction flask was degassed with argon for 1 hour and immersed in a 60° C. oil bath. The polymerization was left to run for a predetermined time. When the polymerization was finished, the solution was precipitated into diethyl ether and centrifuged. The precipitate was re-dissolved in DCM, precipitated in diethyl ether and centrifuged again. This process was repeated twice. Finally, the polymer was dried under reduced pressure overnight.

Figure 2:
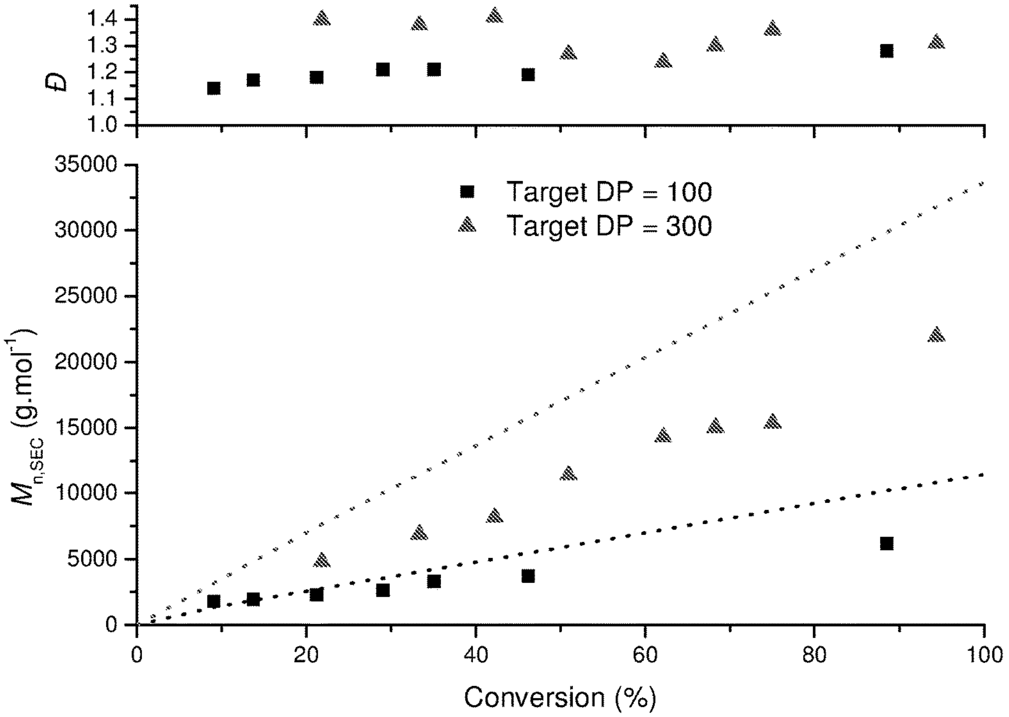
FIG. 2 shows the conversion plot for poly(N-vinylpyrrolidone) (PVP) synthesis using RAFT agent 4.

Two molar mass poly(N-vinylpyrrolidone) (PVP) polymers were synthesised, DP=100 and DP=300, respectively. A conversion study was performed to determine whether RAFT agent 4 controlled the polymerisation of PVP. The solid data points represent the experimental data and the dotted lines represent the theoretical molar mass (FIG. 2). It is clear that in both cases, molar mass increases linearly over time. The difference between the theoretical and experimental molar mass is due to the difference in hydrodynamic volumes between PVP and the poly(methyl methacrylate) that was used in the molar mass analysis.

The data from the conversion study allowed molar masses to be targeted more accurately. Using this information, two PVP polymers were synthesised (Table 1).

TABLE 1

Data for PVP polymers (5, 6) synthesised in this study

| # | DP | $\alpha^a$ (%) | Reaction Time (hr) | Reaction Temp (° C.) | $M_{n, theo}$, (g/mol) | $M_{n, SEC}{}^b$ (g/mol) | $M_{n,NMR}{}^c$ (g/mol) | Đ |
|---|---|---|---|---|---|---|---|---|
| 5 | 50 | 60 | 20 | 60 | 3700 | 2700 | 3900 | 1.24 |
| 6 | 100 | 60 | 20 | 60 | 7000 | 5300 | 7300 | 1.16 |

[a]conversion

[b]$M_{n,SEC}$ based on PMMA standards

Figure 3:
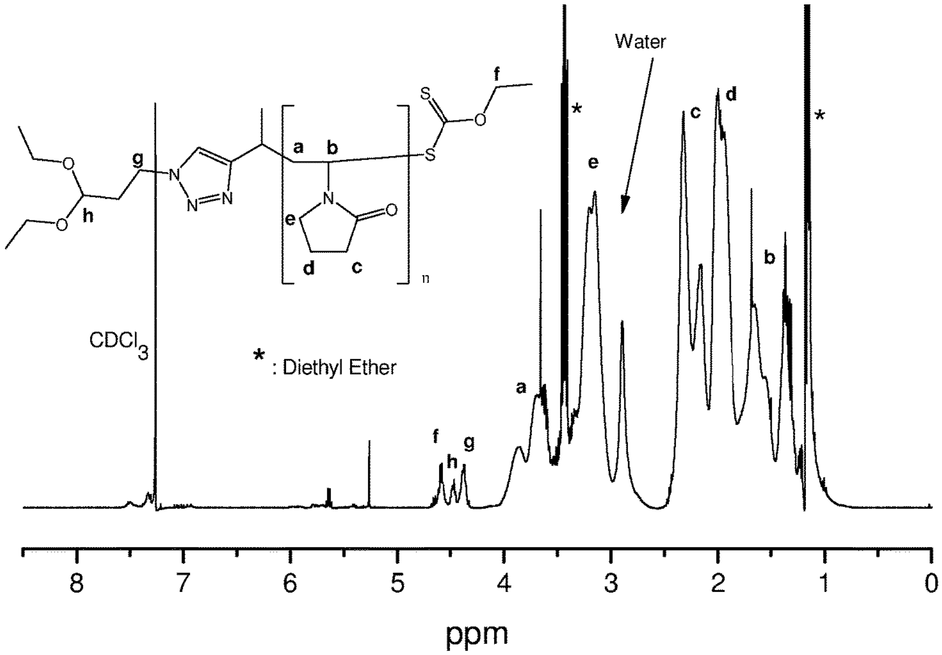
FIG. 3 shows the $^1$H NMR spectrum of polymer 5.

[c]$M_{n,NMR}$ determined by integrating the xanthate signal versus the polymer backbone signal $^1H$ NMR was performed to determine whether the polymers 5 and 6 still contained end-group functionality. It can be seen in FIG. 3, which shows the $^1H$ NMR spectrum of polymer 5, that proton f from the xanthate was integrated against protons g and h from the acetal functionality and were found to be present in a 1:1 ratio. This confirmed that every polymer chain had both the acetal and xanthate moieties attached. The same held true for 6.

2. Cleaving of the Protected Functionalities on PVP

Polymers 5 and 6 both retained their end-group functionality, an acetal and a xanthate. It is known that acetals can be deprotected to form aldehydes under acidic conditions,[3] that xanthates can be cleaved to thiols under reducing conditions,[4] and that thiols form disulfides under oxidising condtions.[5] In the present study, the deprotection was performed in one step insitu (Scheme 3). The acetal and xanthate functionalities were cleaved in a one pot process by dissolving the PVP in acetone and adding a 3 times excess hexylamine. This was left to react for 4 hours, after which HCl in dioxane (4 M) was added until the overall concentration was 1 M HCl. This was left to react for an additional 4 hours. The solution was dialysed in 2000 molecular weight cutoff dialysis tubing for 2 days against a water/methanol (1:1) solution and for 1 day against water, after which it was freeze dried yielding polymers 7 and 8, respectively.

Scheme 3 - One-pot deprotection of PVP system

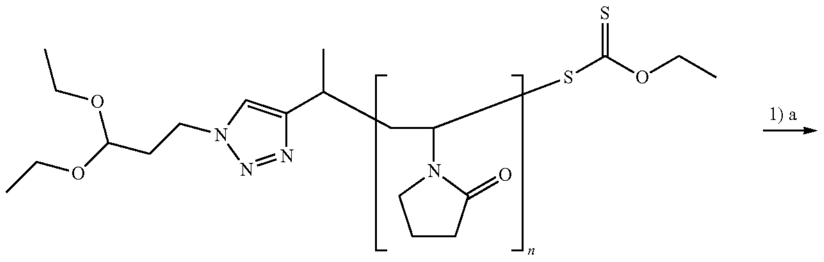

-continued

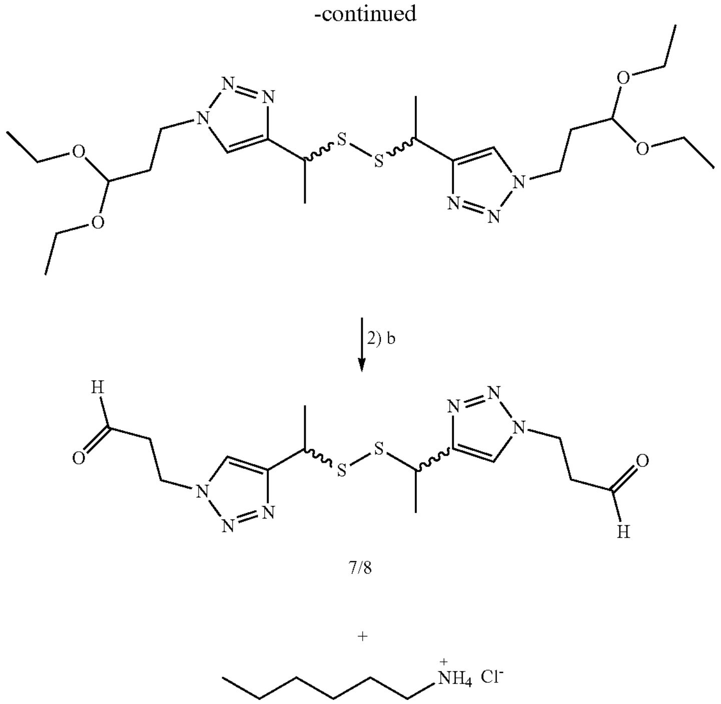

7/8

(a) hexylamine, acetone, r.t.; (b) 4M HCl in dioxane, acetone

Figure 5:
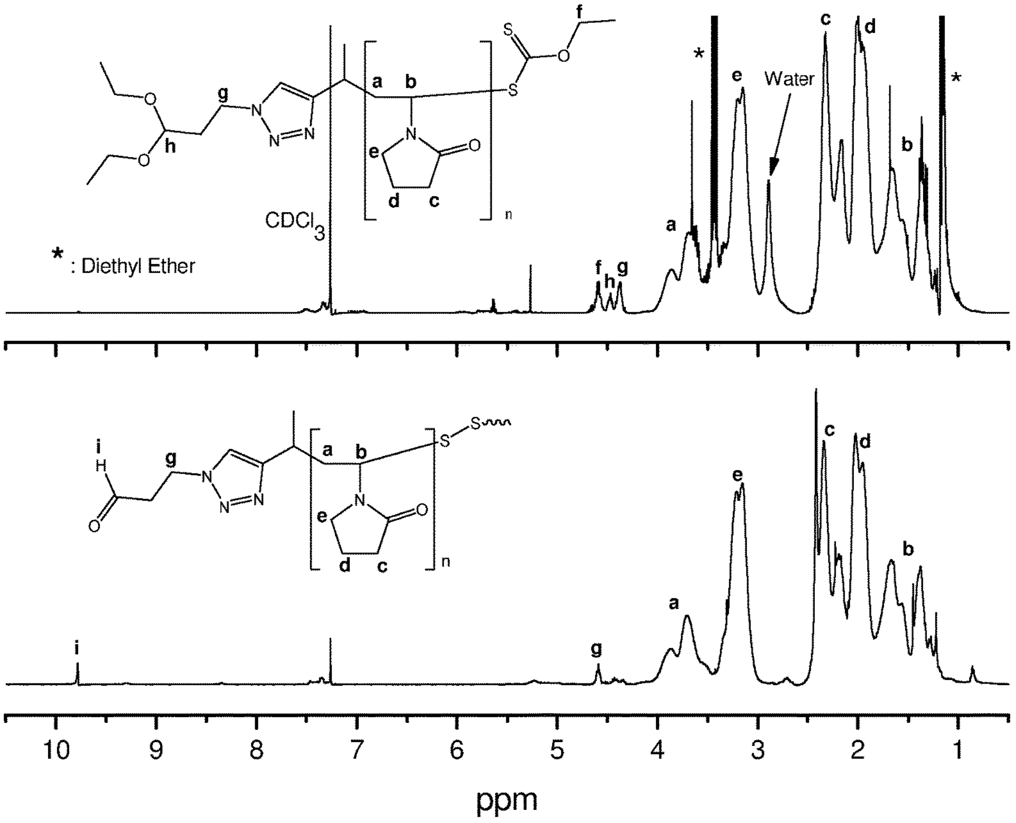
FIG. 5 shows one-pot deprotection of polymer 5 to yield polymer 7.
Figure 6:
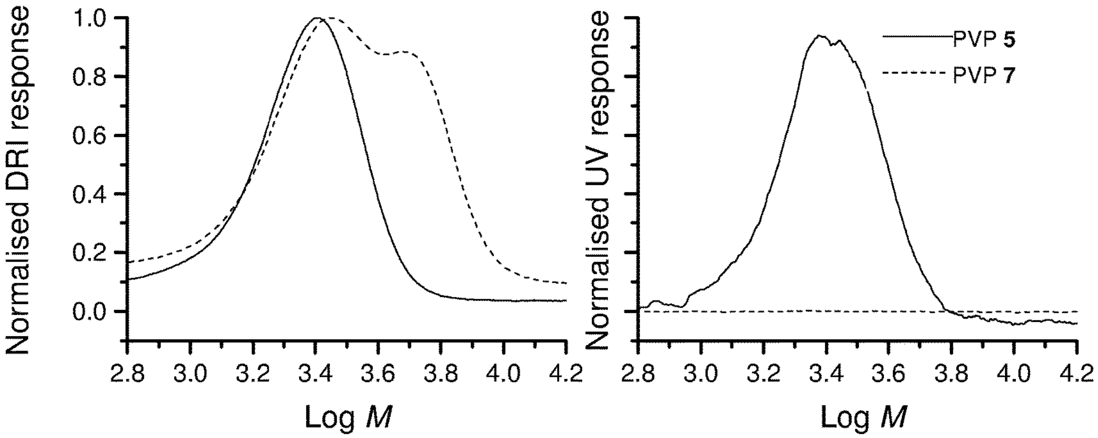
FIG. 6 shows DRI and UV SEC molar mass distribution comparing polymer 5 to polymer 7.

$^1$H NMR spectroscopy confirmed the presence of the aldehydic proton i at 9.79 ppm, the loss of protons h at 4.48 ppm, ascribed to the acetal moiety, and the loss of protons f at 4.58 ppm, attributed to the xanthate moiety (FIG. 5). Although most structural information was derived from $^1$H NMR spectroscopy, it was not possible to ascertain the extent of disulphide formation. It was expected that there would be a distribution of both free thiols and disulphides, and SEC was used to determine the extent of this. Disulphide formation is observed as a doubling of molar mass, which can be seen as a shoulder in the chromatogram (FIG. 6). In addition, the UV (280 nm) signal, attributed to absorbance by the xanthate functionality, was also recorded and it was clear that no xanthate moieties were still present in PVP 7. PVP 6 (5300 g·mol$^{-1}$) was deprotected in a similar fashion to yield 8.

General One-Pot Deprotection of PVP End-Groups (7)

5 (2.50 g, 0.926 mmol aldehyde), hexylamine (0.281 g, 2.78 mmol) and acetone (13.9 mL) were introduced to a 50 mL round bottom flask and stirred for 4 hours at room temperature. HCl (13.9 mL, 4 M in dioxane) was added, to bring the overall HCl concentration to 1 M, and the reaction was stirred for an additional 4 hours at room temperature. The solution was purified via dialysis (2000 Da MWCO) against water/methanol (1:1) for 2 days and pure water for an additional day, after which the product was freeze-dried to obtain 7 as a white powder. End-group analysis was performed via $^1$H NMR spectroscopy, and molar mass and dispersity were determined via SEC.

3. Conjugation of Polymers to a Targeting Ligand

Figure 7:
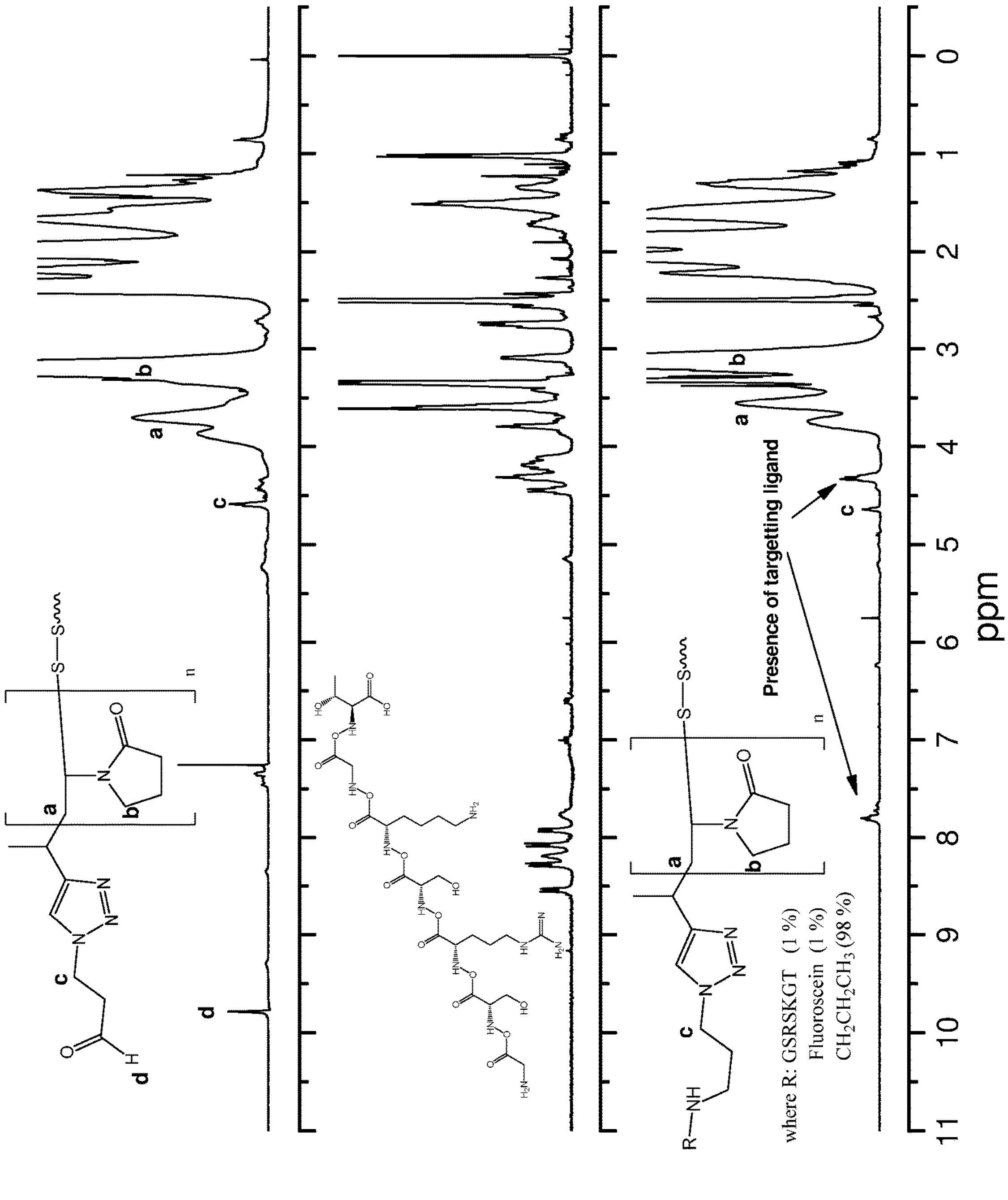
FIG. 7 shows targeting ligand incorporation in polymer 7 to yield polymer 9.

Polymers 7 and 8 were reacted with Gly-Ser-Arg-Ser-Lys-Gly-Thr (SEQ ID NO: 178) (2% mole equivalence) from GL Biochem, 6-aminofluoroscein (2% mole equivalence) and $NaBH_3CN$ (10×excess) in sodium borate buffer (pH 9.7) overnight. 200% propylamine was added the following day to render the remaining aldehyde groups inactive (Scheme 4). The solution was dialysed again in 2000 g/mol molecular weight cutoff dialysis tubing for three days against water and subsequently freeze dried to yield polymers 9 and 10, respectively. $^1$H NMR confirmed the functionalization (FIG. 7). Although it was not possible to assign the $^1$H NMR of the epitope, it is clear that it is incorporated in the PVP. It is also clear that the aldehyde proton present at 10 ppm disappears.

Scheme 4 - Conjugation of targeting ligand to 7 and 8

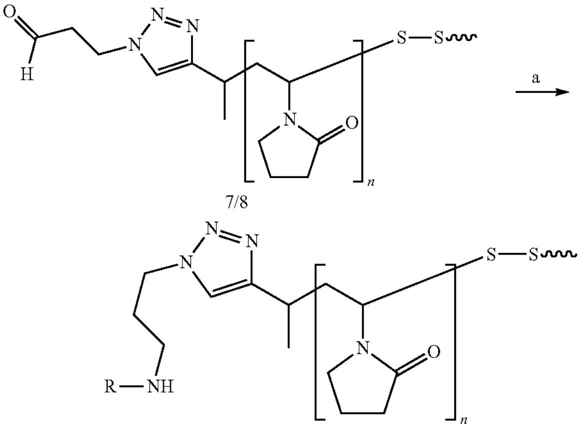

7/8

9/10 where R: GSRSKGT (1%)
Fluorescein (1%)
$CH_2CH_2CH_3$ (98%)

(a) GSRSKGT, 6-aminofluorescein, n-propylamine, $NaBH_3CN$, sodium borate buffer (pH = 9.7), r.t.

Figure 8:
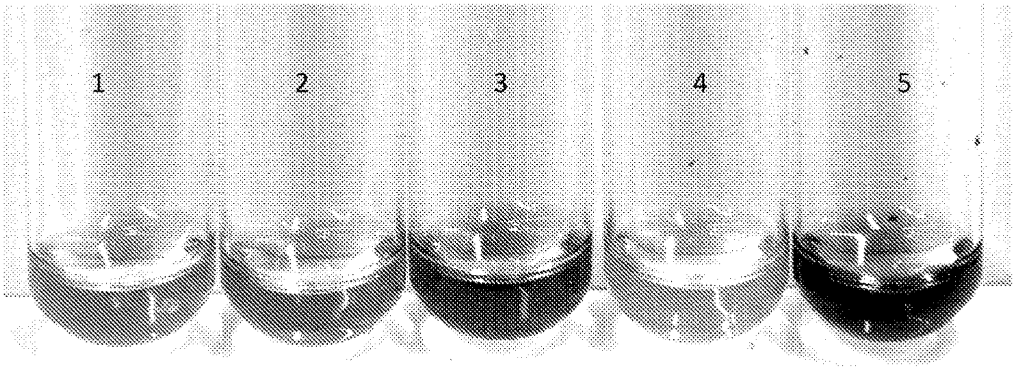
FIG. 8 shows positive Kaiser test results of polymer 9 and 10 ((1) Control—DMF and reagents; (2) PVP 8—control; (3) PVP 10; (4) PVP 7—control; (5) PVP 9)

In order to further clarify the presence of the targeting ligand GSRSKGT (SEQ ID NO: 178) within polymers 9 and 10, a qualitative Kaiser test was performed, which tests for the presence of primary amines. The only source of primary amines within 9 and 10 was as a result of the ε-amine within the lysine residue (K) of Gly-Ser-Arg-Ser-Lys-Gly-Thr (SEQ ID NO: 178)(FOG. 8). A positive Kaiser test result is a blue to green colour, while a negative result should remain yellow. FIG. 8 shows the Kaiser test results, confirming that Gly-Ser-Arg-Ser-Lys-Gly-Thr (SEQ ID NO: 178) forms part of PVP 9 and PVP 10. Test tube 1 contains the Kaiser test reagents and DMF, as a control. Test tubes 2 and 4 comprise terminal aldehyde polymers 8 and 7 (no primary amine residues) with the Kaiser reagents, respectively, as a control. Test tubes 3 and 5 contain the Kaiser reagents together with polymers 10 and 9, respectively. In all three control reactions (test tubes 1, 2 and 4), the colour remained yellow, affirming that no primary amines were present. However, test tubes 3 and 5 gave a positive result for the presence of primary amines. The colour was less intense in test tube 3—as a result of the higher molar mass PVP 10, a lower ratio of primary amines was present. The Kaiser test, although used in a qualitative nature, proved the presence of the targeting ligand within PVP 9 and 10.

General Synthesis of Targeting Ligand-Terminal PVP (9)

NaOH (400 mg, 10.0 mmol) was dissolved in water and made up to 100 mL in a volumetric flask (0.1 M, solution A). In parallel, sodium borate (1.02 g, 5.00 mmol) was dissolved in water and made up to 100 mL in a volumetric flask (50.0 mM, solution B). Solution A (32.3 mL) was placed in a 100 mL volumetric flask and made up to 100 mL using solution B, affording a sodium borate buffer (pH=9.7). 6-Aminofluorescein (4.13 mg, 11.9 μmol) was dissolved in sodium borate buffer (1 mL, pH=9.7) to afford a 6-minofluorescein stock solution (11.9 mM). PVP 7 (0.321 g, 0.119 mmol), Gly-Ser-Arg-Ser-Lys-Gly-Thr (2.00 mg, 2.38 μmol), 6-aminofluoroscein stock solution (200 μL, 2.38 μmol), $NaBH_3CN$ (74.8 mg, 1.19 mmol) and sodium borate buffer (2 mL, pH=9.7) were introduced to a 10 mL round bottom flask and placed on a shaker overnight at room temperature. n-Propylamine (14.1 mg, 23.8 μmol) was added and the solution was shaken for a subsequent 4 hours, after which it was dialysed (2000 Da MWCO) against water for 2 days and freeze-dried to afford a white powder, 9.

4. Synthesis of Acrylate Functionalised-Tyrocidine

Synthesis of Acrylate-Modifed Tyrocidine a) Acryloyl chloride (0.0278 g, $3.08\times10^{-4}$ mol) and DMF (5 mL) were added to a 20 mL sample flask and cooled to 0° C. in an ice bath. Tyrocidine (0.020 g, $1.5\times10^{-5}$ mol), Dimethylformamide (2 mL) and N,N-Diisopropylethylamine (0.038 g, $3.1\times10^{-4}$ mol) were mixed in a 20 mL container and this mixture was then slowly added dropwise into the sample flask over 30 minutes. The reaction was left to mix over 48 hours on a shaker in a 4° C. room. The DMF was removed via rotorvap and the residue was dissolved in 500 μL ethanol. This was subsequently precipitated in diethyl ether/acetone (6:4, 20 mL). The precipitate was centrifuged and this was repeated twice to yield acrylate functionalised Tyrocidine (Scheme 5).

b) The above method was also repeated on a larger scale a follows: A 100 mL round bottom flask was charged with acryloyl chloride (78.3 μL, 0.969 mmol) and DMF (80 mL) and cooled to 0° C. in an ice bath. Tyrocidine (63.0 mg, 48.5 μmol) and DIPEA (169 μL, 0.969 mmol) were dissolved in DMF (10 mL) and added dropwise to the round bottom flask over 30 minutes. The round bottom flask was placed on a shaker in a 4° C. room and left to react for 2 days, after which the solution was concentrated. The remaining residue was redissolved in ethanol (500 μL) and precipitated in diethyl ether/acetone (3:2) and the mixture was subsequently centrifuged. The pellet was washed with diethyl ether/acetone (3:2) and centrifuged, and the process was repeated twice. The pellet was dissolved in 50% MeCN and freeze-dried (49.2 mg, 75%) (Scheme 5).

Scheme 5 - Functionalisation of Tyrocidine

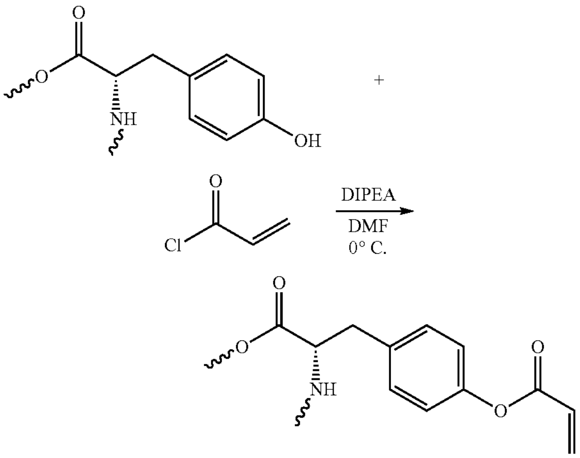

Figure 9:
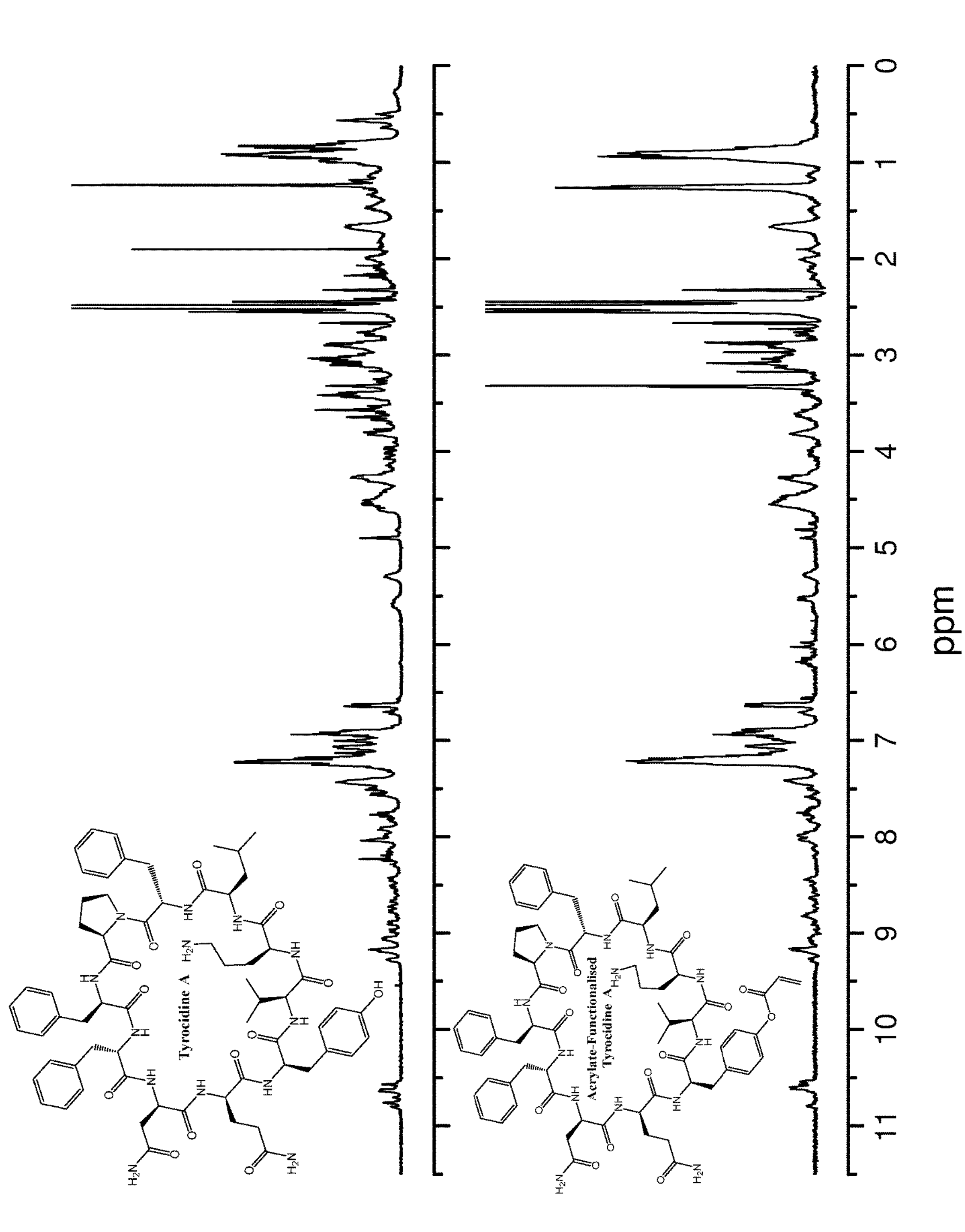
FIG. 9 shows the functionalisation of Tyrocidine.
Figure 10:
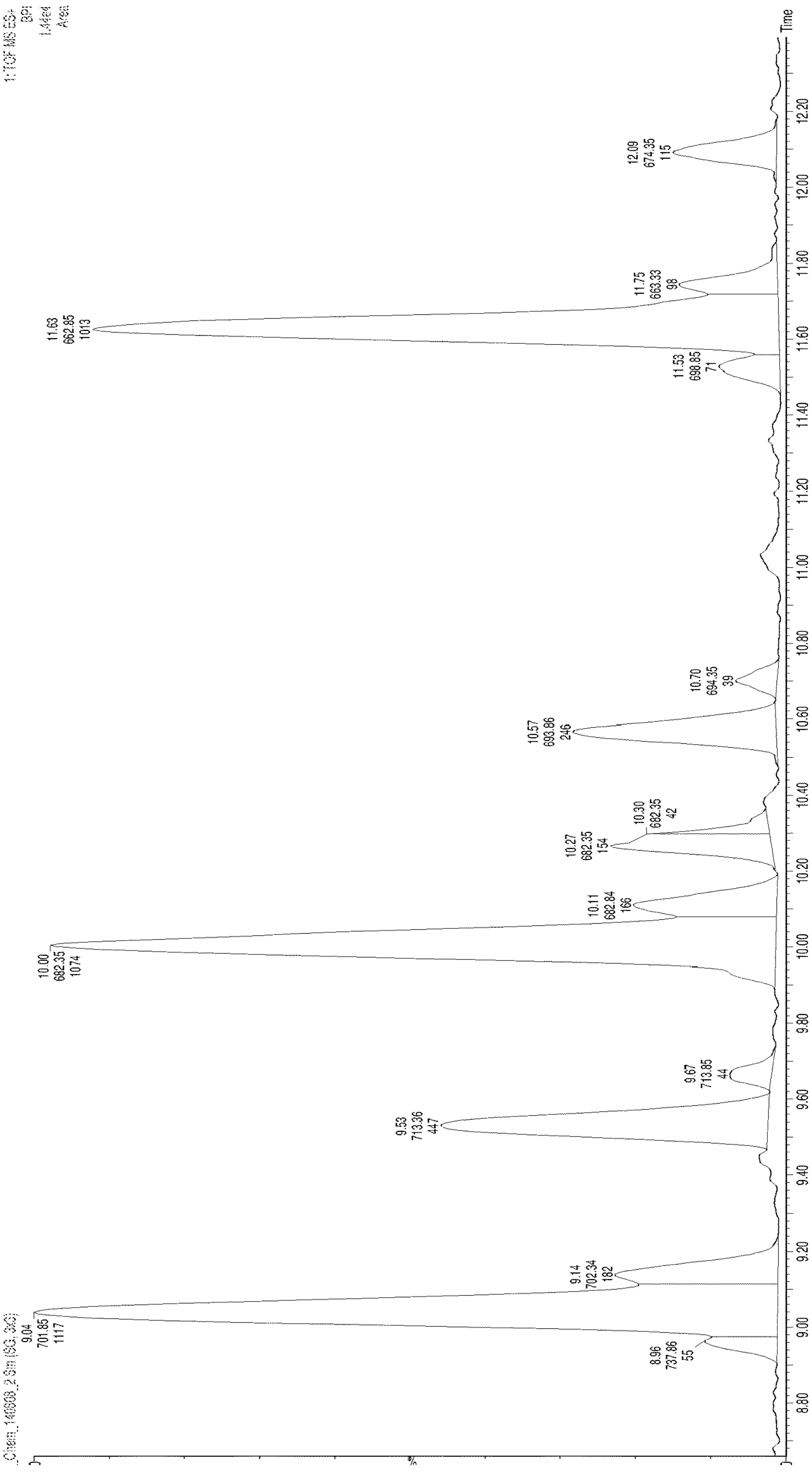
FIG. 10 shows a chromatogram (LC-MS) of modified Tyrocidine mixture.
Figure 11:
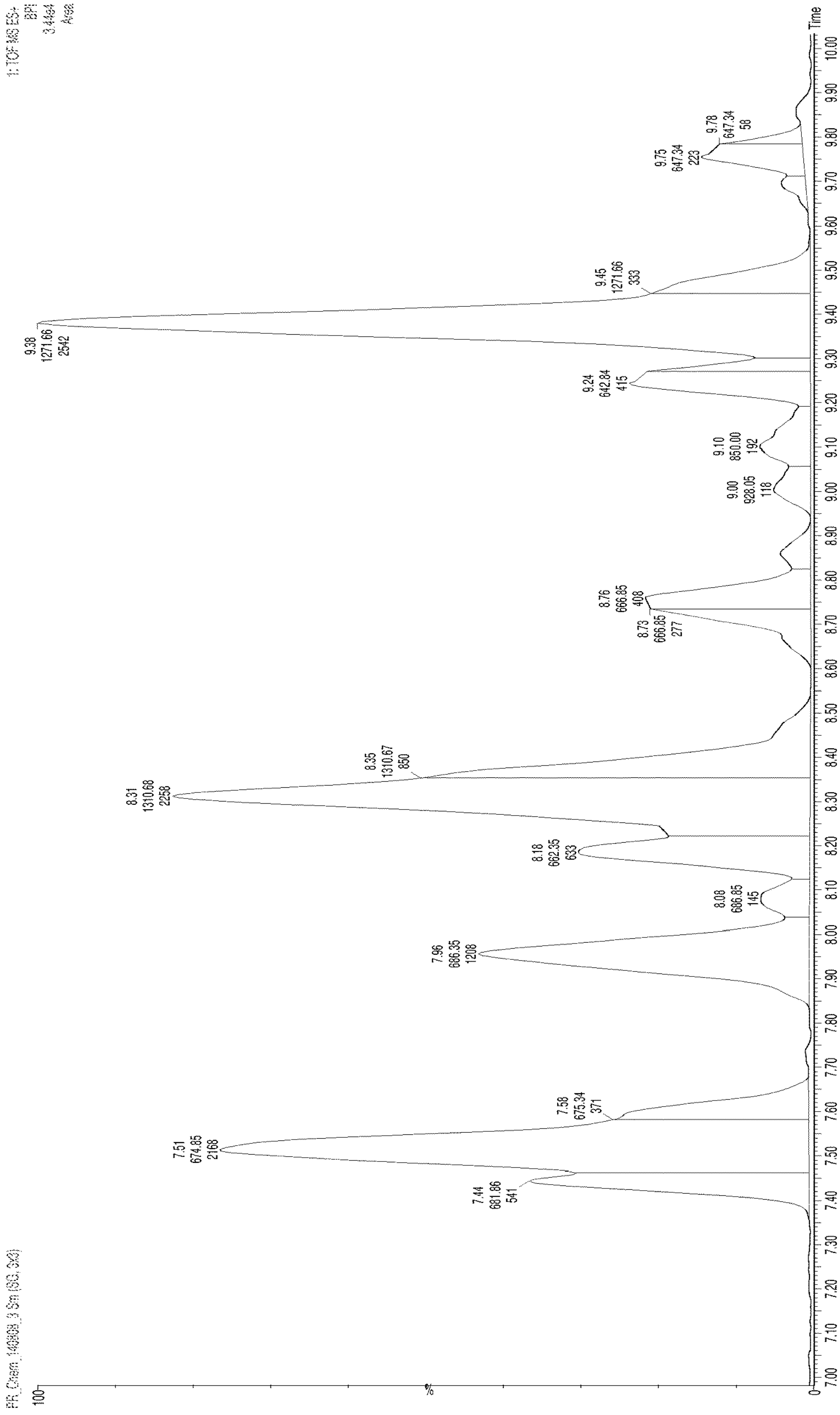
FIG. 11 shows a chromatogram (LC-MS) of unmodified Tyrocidine mixture.

Mass spectrometry and $^1H$ NMR were used to confirm the structure (FIG. 9). Although it is not possible to assign the spectrum, it is possible to observe the presence of the olefinic (acrylate) protons between 5.5 and 6.5 ppm. Mass spectrometry confirmed the presence of the functionalised tyrocidines. These natural cyclodecapeptides were produced via bacterial cultures (Vosloo et al.) and as a result the cyclodecapeptides contain tyrocidine A, B and C and also a small amount of tryptocidine A, B and C. Mass spectrometry confirmed that the tryptocidines were also functionalised via an acrylamide bond to the Orn or Lys residue (FIGS. 9 and 10, Tables 2 and 3).

TABLE 2

Percent composition of modified Tyrocidine mixture as derived from LC-MS

| RT | Peak area | % contribution | Tyr mod | Orn mod | Lys mod |
|---|---|---|---|---|---|
| 8.964 | 54.982 | 1.13 | | | |
| 9.039 | 1116.907 | 22.97 | TrcC | | |
| 9.14 | 182.368 | 3.75 | $TrcC_1$ | | |
| 9.529 | 447.289 | 9.20 | | TpcC | |
| 9.668 | 43.681 | 0.90 | | TpcC | |
| 10.005 | 1073.949 | 22.09 | TrcB | | |
| 10.109 | 165.87 | 3.41 | TrcB' | | |
| 10.267 | 153.689 | 3.16 | $TrcB_1$ | | |
| 10.297 | 41.72 | 0.86 | $TrcB_1$' | | |
| 10.566 | 246.357 | 5.07 | | TpcB | |
| 10.701 | 39.03 | 0.80 | | TpcB' | |
| 11.529 | 70.713 | 1.45 | | | $TpcB_1$ |
| 11.626 | 1012.674 | 20.83 | TrcA | | |
| 11.746 | 98.241 | 2.02 | $TrcA_1$ | | |
| 12.09 | 114.9 | 2.36 | | TpcA | |
| | 4862.37 | | | | |
| | | % contribution | 74.82 | 24.05 | |

Assumption - modified Tpcs and Trcs have similar ionisation properties

TABLE 3

Percent composition of unmodified Tyrocidine mixture as derived from LC-MS

| Rt | Area | Identity | % contribution | |
|---|---|---|---|---|
| 7.444 | 541.018 | $TrcC_1$ | 4.26 | |
| 7.515 | 2167.804 | TrcC | 17.07 | 20.00 |
| 7.582 | 371.191 | TrcC | 2.92 | |
| 7.956 | 1208.249 | TpcC | 9.52 | |
| 8.08 | 144.614 | TpcC | 1.14 | |
| 8.184 | 633.481 | $TrcB_1$ | 4.99 | |
| 8.312 | 2258.5 | TrcB | 17.79 | 24.48 |
| 8.353 | 850.028 | TrcB' | 6.70 | |
| 8.735 | 277.205 | TpcB' | 2.18 | |
| 8.758 | 407.733 | TpcB | 3.21 | |
| 8.859 | 81.69 | $TpcB_1$ | 0.64 | |
| 9.244 | 414.596 | $TrcA_1$ | 3.27 | |
| 9.271 | 135.135 | $TrcA_1$ | 1.06 | |
| 9.379 | 2542.415 | TrcA | 20.02 | 22.65 |
| 9.447 | 333.374 | TrcA | 2.63 | |
| 9.697 | 47.727 | PhcA | 0.38 | |
| 9.753 | 223.331 | TpcA | 1.76 | |
| 9.784 | 58.238 | TpcA | 0.46 | |
| | 12696.329 | | | |

Assumption - Tpcs and Trcs have similar ionisation properties

5. Conjugation of Polymers to Acrylate-Functionalised Tyrocidine

Polymers 9 and 10 were conjugated to the acrylate-functionalised Tyrocidine through Michael Addition (Scheme 6). Thiols react with acrylates[7] and acrylamides to form a β-thiopropionate and β-thiopropioamide linker respectively, which is acid-labile at pH 5.5 but stable within the blood (pH 7.4).[8] This will allow the release of the Tyrocidine after administration to a patient and being taken up in the food vacuole of the parasite (pH 5.5).

Scheme 6 - Synthesis of targeting ligand-PVP-tyrocidine conjugate

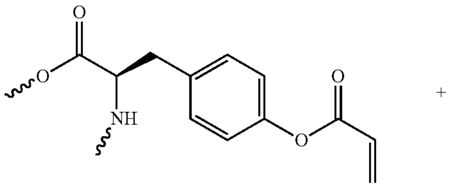

where R: GSRSKGT (1%)
Fluorescein (1%)
$CH_2CH_2CH_3$ (98%)

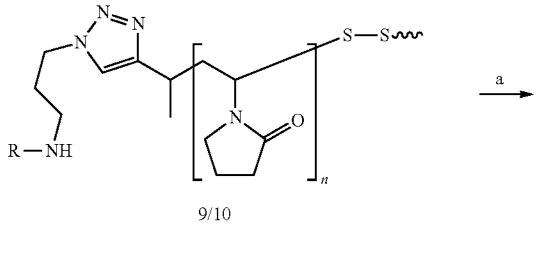

9/10

-continued

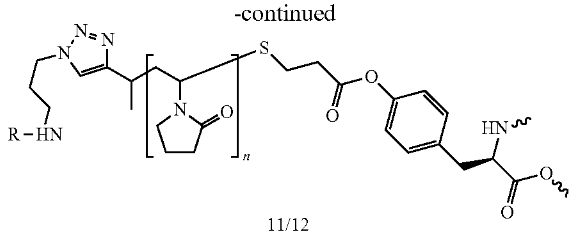

11/12 where R: GSRSKGT (1%)
Fluorescein (1%)
$CH_2CH_2CH_3$ (98%)

(a) TCEP, ethylene diamine, DMF, r.t.

General Synthesis of Conjugate (9/10)

a) In one experiment, PVP 9/10 and acrylate-functionalised Tyrocidine were dissolved in DMF/Water (1:1) and treated with an excess tris(2-carboxyethyl) phosphine (TCEP solution (0.5 M, pH 7.0), 10× excess) and a catalytic amount of Ethylene diamine (1%) and left to react for 3 days. Water was added slowly, via syringe pump, to induce self-assembly. The respective solutions were dialysed in 10 000 molecular weight cutoff dialysis tubing for 2 days to remove DMF, unreacted polymer and Tyrocidines.

b) In another experiment, ethylene diamine (10.0 mg, 166 μmol) was dissolved in water (20 mL) to afford an ethylene diamine stock solution (8.3 mM). PVP 9/10 (10.0 mg, 3.7 μmol), tyrocidine mixture (4.81 mg, 3.70 μmol), TCEP solution (7.5 μL, 37 μmol, 0.5 M, pH=7.0), ethylene diamine stock solution (4 μL, 37.0 μmol), water (500 μL) and DMF (500 μL) were introduced to a 50 mL round bottom flask and placed on a shaker at room temperature for 24 hours. Water (30 mL) was introduced via a syringe pump, over 1 hour, to facilitate self-assembly. The solution was purified by dialysis (2000 Da MWCO) against water for 2 days and further dialysis using a higher MWCO (10000 Da) for a further day, to afford a milky dispersion 11/12.

Figure 12:
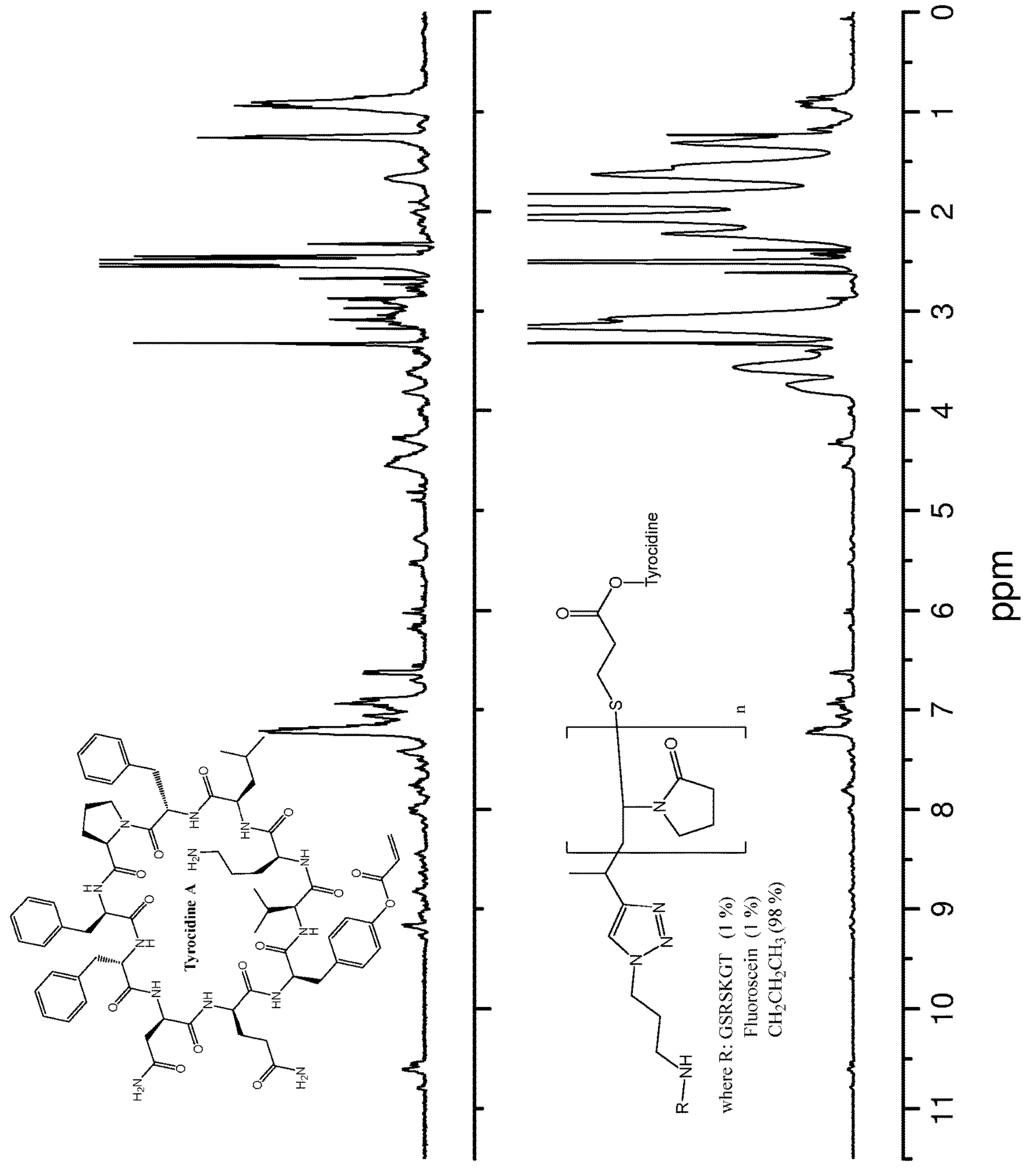
FIG. 12 shows the $^1$H NMR for the Tyrocidine-PVP-target ligand conjugate.
Figure 13:
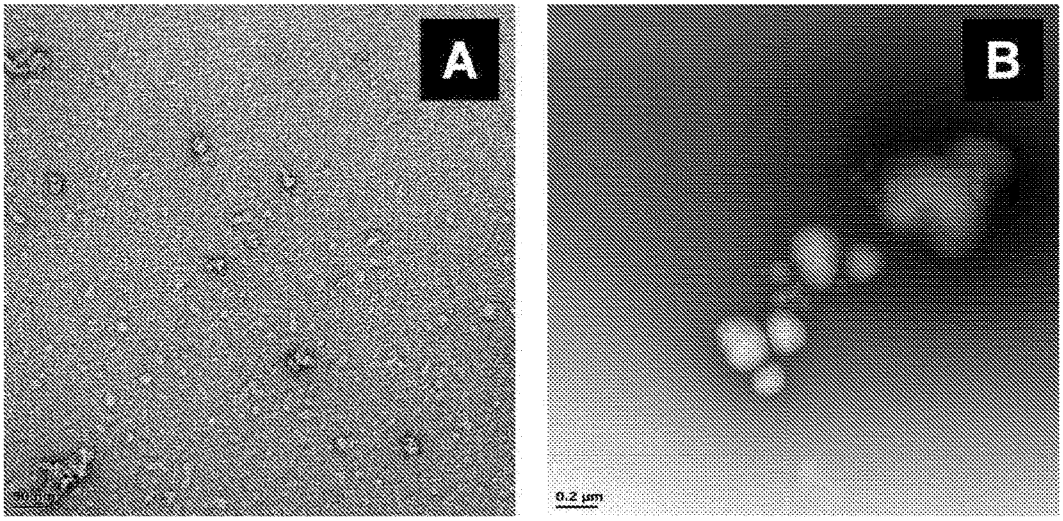
FIG. 13 shows a transmission electron microscope image of Tyrocidine-PVP-target ligand conjugate 11(a) and 12(b)

$^1$H NMR confirmed functionalization (FIG. 12). It is not possible to assign the spectrum but the presence of the Tyrocidine is clearly visible. TEM was used to visualise the distribution of particle size (FIG. 13). Conjugate 11 (a) and average particle sizes of 10-20 nm were observed. However, aggregation was also present. Conjugate 12 (b) had much larger particle sizes, ranging from 20 nm to aggregates of 600 nm. It was concluded that the hydrophilic lower mass PVP polymer 9 ($M_n$=2700 g·mol$^{-1}$) stabilised the aggregation-prone tyrocidine ($M_n$=~1300 g·mol$^{-1}$) better than the higher molar mass PVP polymer 10 (5300 g·mol$^{-1}$—thiol chain ends).

6. Tyrocidine/Tryptocidine Release Studies

Figure 14:
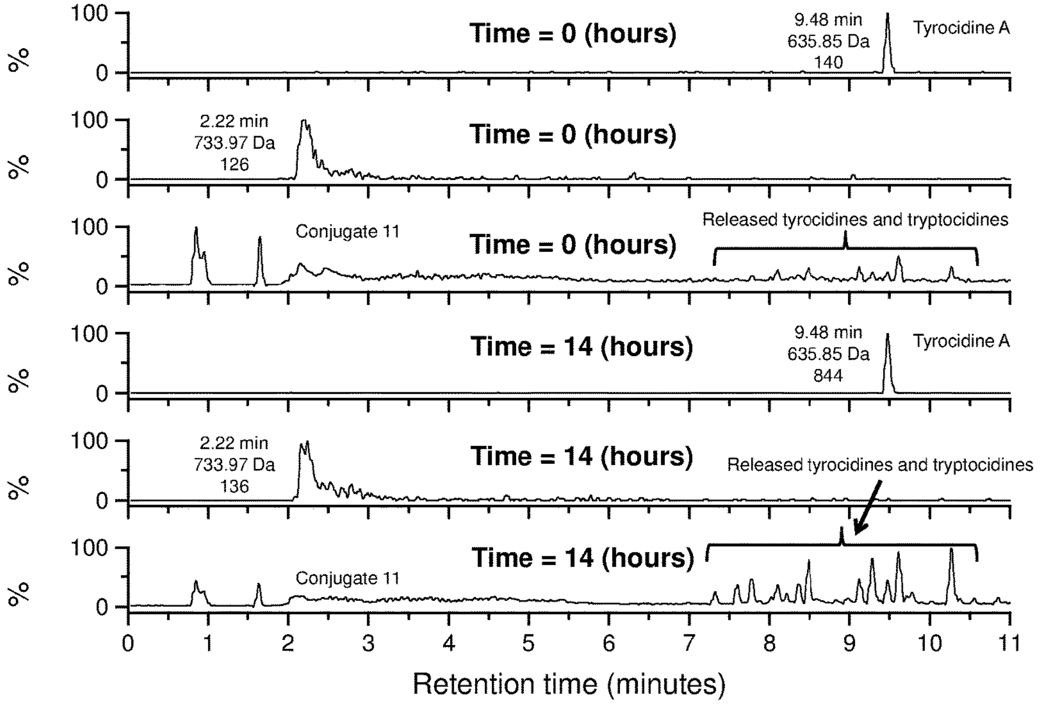
FIG. 14 shows release of tyrocidine from conjugate 11 over time, in a phosphate buffer (pH=5.5)

A qualitative study was performed on the release of the tyrocidines over time, via UPLC-MS, to confirm that the acid-labile linkage between the tyrocidines linker and PVP cleaved under acidic conditions over 24 hours. A 1 mL sample of 11 was freeze-dried and redissolved in a phosphate buffer (pH=5.5). Samples were taken initially and again after 3 hours, 6 hours, 12 hours and 14 hours, and were immediately frozen in liquid nitrogen and subsequently stored in the freezer until analysis. Normally, matrix-assisted laser desorption/ionisation time-of-flight (MALDI-TOF) mass spectroscopy (MS) is needed to visualise polymers above 3000 g·mol$^{-1}$. However, as a result of the PVP being conjugated to the tyrocidines, they were found to ionise easily under normal MS conditions. FIG. 14 shows the release studies at inception and after 14 hours for the conjugate 11.

Three chromatograms were chosen for each time period. The average molar mass of conjugate 11 was 4000 $g \cdot mol^{-1}$ and multiple distributions were present. However, a penta-charged molecular ion was chosen to represent the conjugate (733.97 Da). TrcA was chosen to represent the released tyrocidines. In each case, the representative peaks were labelled with their retention time, mass-to-charge ratio (m/z) and molecular ion count. The spectra shown at 0 hours were not an absolute control, as time was taken for the sample to thaw prior to injection onto the UPLC-MS. This attributed to released tyrocidines and tryptocidines being seen in these spectra. It is clear that from inception to 14 hours, the count of tyrocidines released over time increased substantially, from 140 to 844, if TrcA release is taken as measure. In addition, visually, the signal intensity at the retention time where the conjugate eluted (2-4 minutes) decreased, and then dramatically increased where the tyrocidines eluted (7-11 minutes), over time.

Figure 15:
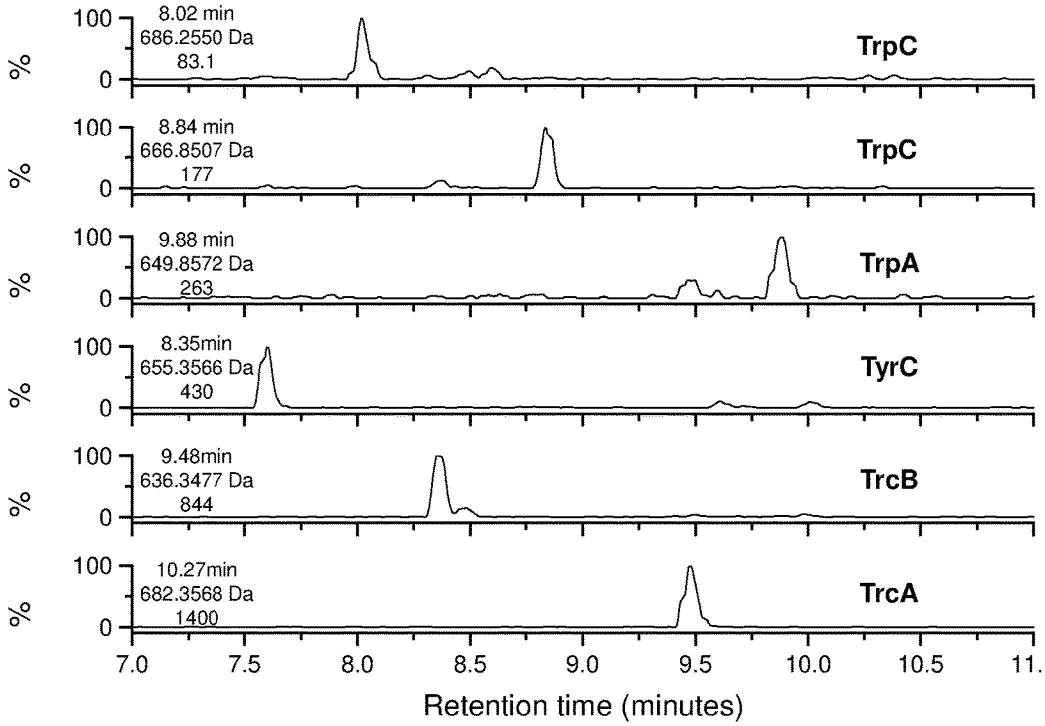
FIG. 15 shows individual components of released tyrocidines and tryptocidines.

FIG. 15 shows a breakdown of the individually released tyrothricin components. Each peak is labelled with its retention time, major m/z (doubly charged) and molecular count. It is clear that the three main tyrocidines were the major species and more importantly, they were released, regaining their original structural state. Often conjugates show a decrease in biological activity due to the conjugation site interfering with the mechanism of the original drug uptake. The three main tryptocidine species were also released in their original structure.

The release study confirms that the tyrocidine/tryptocidine conjugates would act as a Trojan-horse drug carrier, releasing the tyrocidines/trptocidines after the conjugate is taken up into malaria-infected erythrocytes.

7. In Vitro Anti-Malaria Assay

Figure 16:
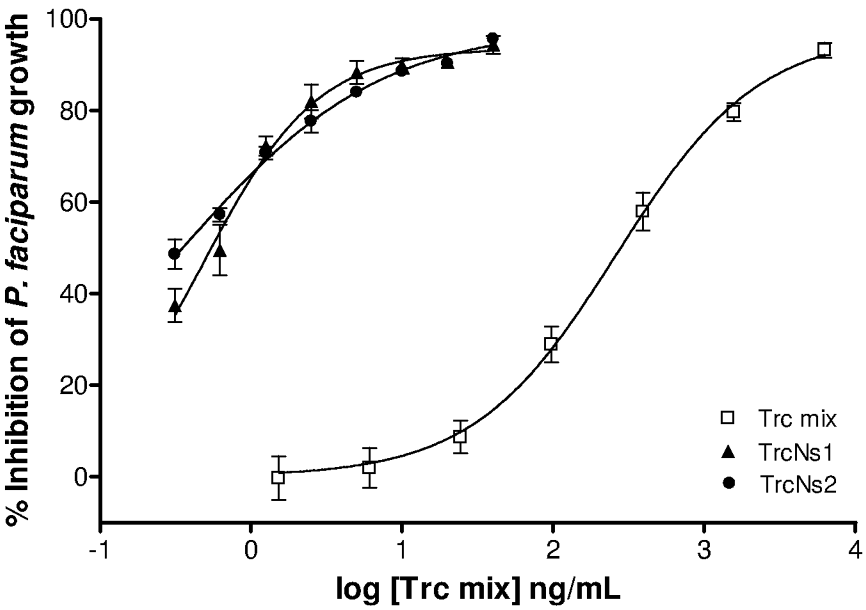
FIG. 16 shows the antimalarial activity of Tyrocidine-PVP-targeting ligand conjugates of the invention in comparison with free Tyrocidine.
Figure 17:
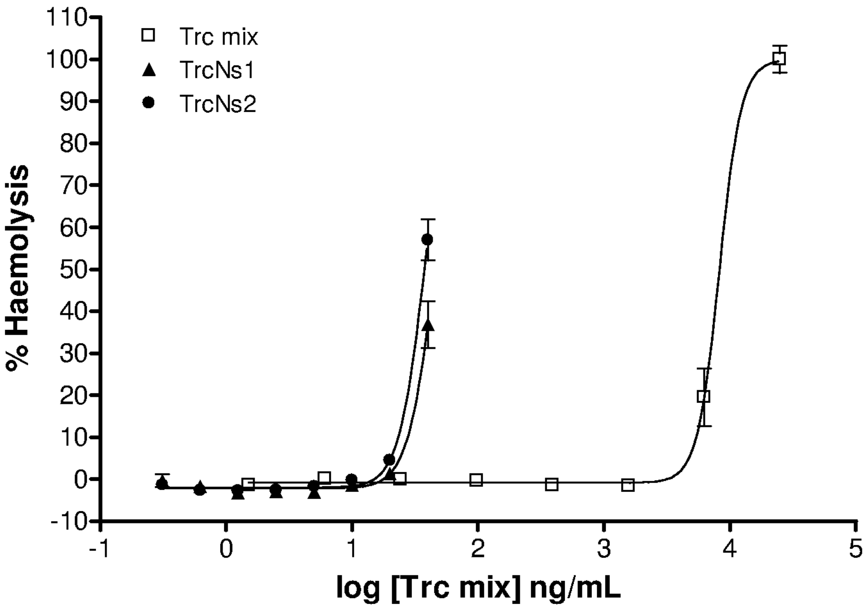
FIG. 17 shows haemolytic activity of Tyrocidine-PVP-target ligand conjugates in comparison with free Tyrocidine.

In separate experiments, tyrocidine/tryptocidines conjugated to polymers 11 and 12, respectively, were administered at varying concentrations to blood samples containing cells infected with a chloroquine-resistant *Plasmodium falciparum* strain (D10 resistant mutant denoted D10R, $IC_{50}$ (chloroquine)>100 nM). For comparison purposes, the unconjugated/unmodified natural tyrocidine/tryptocidine mixture was also administered to blood infected with the same chloroquin-resistant malaria strain. FIGS. 16 and 17 show the antimalaria activity and the haemolytic activity of the tyrocidine/tryptocidine-PVP conjugates in comparison with the natural cyclodecapetide mixture. Both of the conjugates killed malaria at a 450 times lower concentration than the natural cyclodecapetide mixture and were also more selective for the infected red blood cells than the natural cyclodecapetide mixture. At a therapeutically active concentration where all the parasites in the red blood cells were killed within 24 hours, healthy red blood cells were unaffected and many of the infected red blood cells remained intact, with only the hemozoin crystal visible in some cases.

Malaria parasites primarily convert glucose to lactate in their energy metabolism and therefore the 48 hour growth assays will lead to accumulation of lactate/lactic acid in the media. As mentioned above, the cyclodecapetide-PVP conjugates used in these experiments contained primarily tyrocidines, but also small amounts of the tryptocidines. It is known that both the tryptocidines and tyrocidines cause haemolysis of red blood cells and because the haemolysis assay was only performed after 48 hours, it is possible that some or all of the haemolytic activity observed in the malaria assay was due to the presence of free tryptocidines and tyrocidines that were released from the conjugate because of the acidification of the media. If this is the case, the cyclodecapeptide-PVP conjugates may have even higher selectivity for the parasite.

Parasite Culturing

*P. falciparum* (D10 strain) was cultured and dose-response assays were performed as previously described.[9] Briefly, parasites were cultured under an atmosphere of 3% $CO_2$, 4% $O_2$ and 93% $N_2$ in RPMI-1640 media, supplemented with 25 mM HEPES, 50 mM glucose, 0.65 mM hypoxanthine, 0.048 mg/mL gentamicin, 0.2% (w/v) $NaHCO_3$, 0.5% (w/v) Albumax II and 2% fresh human $O^+$ erythrocytes obtained from anonymous donors from the Western Cape Blood Blank. Fresh erythrocytes and media were mixed with the parasitised erythrocytes to yield a 2% haemotocrit and 2% parasitemia suspension, which were distributed in microtitre plates at 90 μL/well. A 10 μL aliquot of a serial double dilution range in media of conjugate 11 and 12 was added into 90 μL of the parasite culture. The plates were incubated under an atmosphere of 3% $CO_2$, 4% $O_2$ and 93% $N_2$ at 37° C. for 48 hours. After incubation, the microtitre plates were centrifuged, to sediment the intact erythrocytes. A 10 μL aliquot from each well was diluted to 100 μL with phosphate buffered saline and analysed at 405 nm, on a plate reader, to determine the quantity of released haemoglobin and haemolytic activity of the conjugates. The remaining culture was then frozen overnight and the parasite survival in each well was determined from the residual lactate dehydrogenase activity, using the Malstat assay.[9] Duplicate plates containing normal erythrocytes (2% haematocrit) were also incubated at 37° C. for 48 hours.

Dose-Response Data Analysis

Triplicate assays were performed for each conjugate against each target cell. The dose-response data was analysed using Graphpad Prism version 3.01 for Windows (GraphPad Software, San Diego, Calif. USA; www.graphpad.com). Percentage parasite viability (lactate dehydrogenase assay) and percentage haemolysis were determined from absorbance values. A non-linear regression (sigmoidal curve with a variable slope) was performed on the dose-response data. Total growth was determined from the control wells (no conjugate added) and total haemolysis, from the addition of 200 μM gramicidin. The 50% *P. falciparium* inhibitory concentration ($IC_{50}$) and the 50% haemolytic concentration ($HC_{50}$) were calculated as described by Rautenbach et al.[9] Apparent selectivity was calculated by the ratio of $HC_{50}$ to $IC_{50}$ and defined as the selectivity index.

8. Microscopy of Conjugate-Treated *P. falciparum* Cultures

Figure 18:
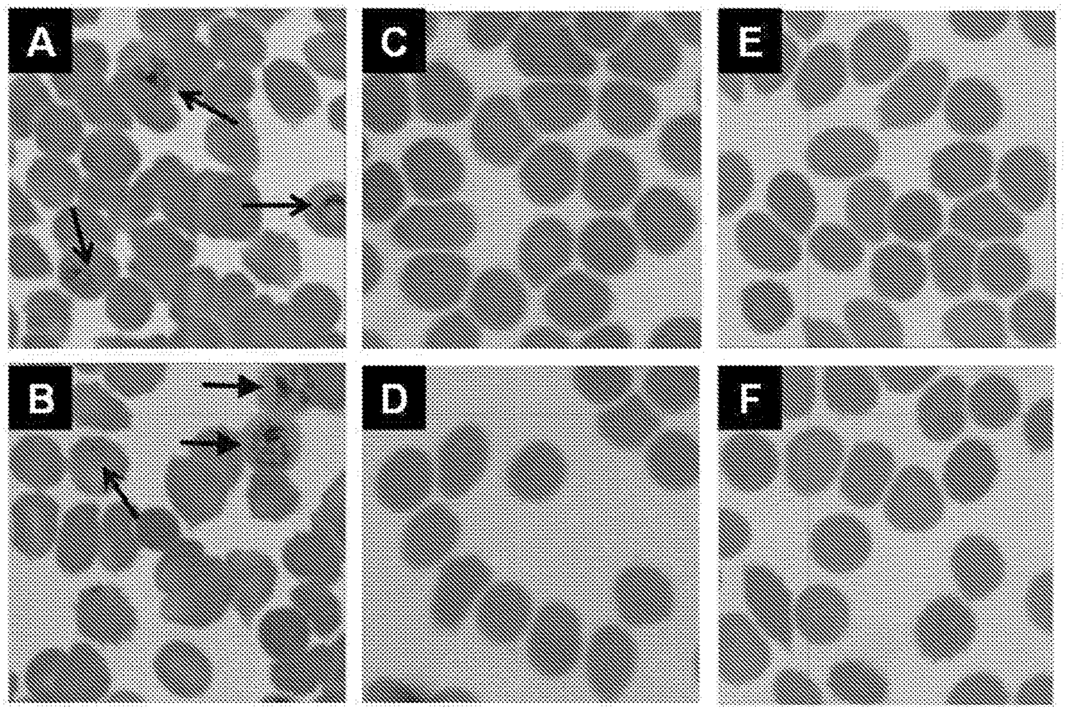
FIG. 18 shows Giemsa-stained blood smears from *P. falciparum* cultures.

Light microscopy was used to study the effect that the tyrocidine-PVP conjugates had on the *P. falciparium* infected erythrocytes. Smears of the conjugate-treated parasite cultures and growth controls were taken at 24 hours and subsequently stained with Giemsa, which stains the malaria parasite purple, to be viewed under the light microscope (FIG. 18). Pictures A and B depict the growth controls after 24 hours and it is possible to see late trophozoites (normal arrow head), schizonts (thick arrow head) and a young ring (stealth arrow head). The growth controls show healthy malarial parasites. Pictures C and D represent malaria-infected erythrocytes that had been treated with 60.4 ng/mL of conjugate 11. It was very clear that no malaria parasite was still alive and that the erythrocytes were healthy and no lysis was present. The same was observed in pictures E and F, where malaria-infected erythrocytes were treated with a 120.8 ng/mL of conjugate 12. Surprisingly, no re-infection or delayed trophozoite growth was observed.[9]

Figure 19:
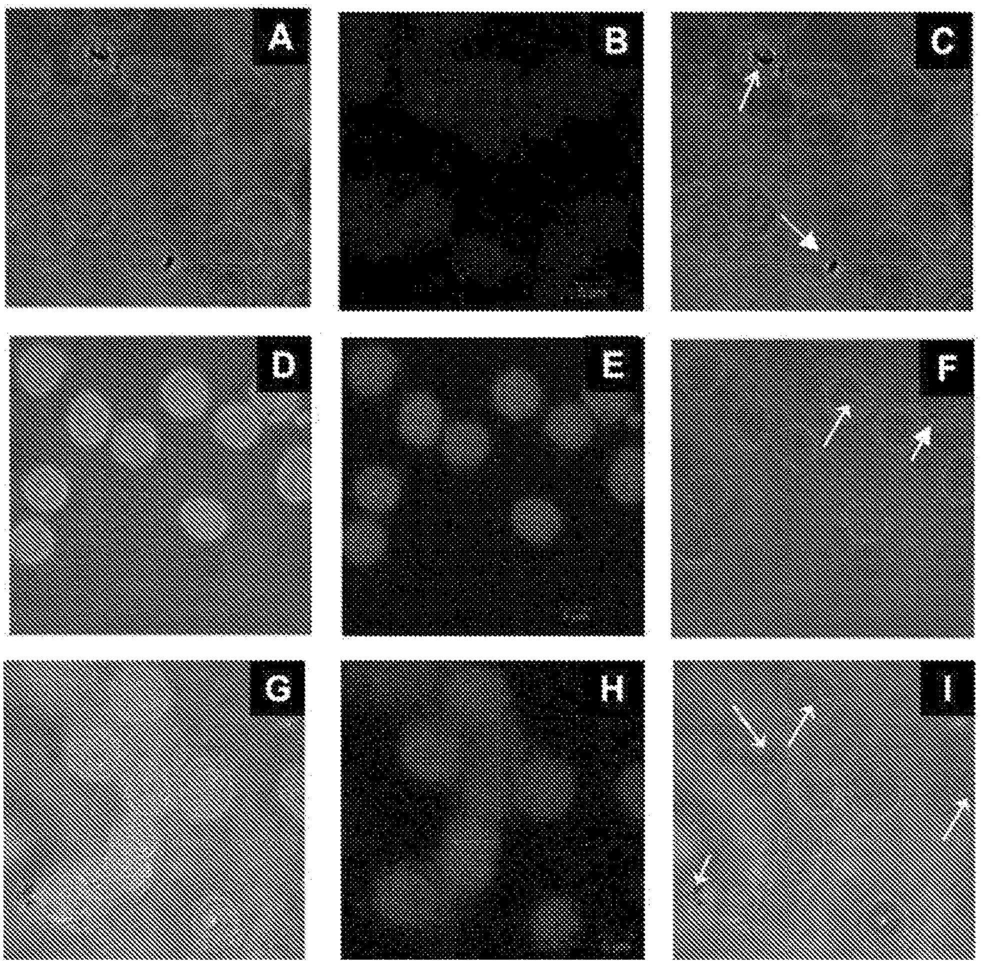
FIG. 19 shows CFM images of the blood smears, taken at 48 hours.

Similarly, smears of the conjugate-treated parasite cultures and growth controls were taken at 48 hours and prepared for confocal fluorescence microscopy (CFM). Conjugates 11 and 12 had been tagged with 1% fluorescein in order to visualise their distribution in the malaria-infected erythrocytes over the normal erythrocytes (FIG. 19). Pictures A, D and G are overlays of the transmission and fluorescence image. Pictures B, E and H are the fluorescence image alone and pictures C, F and I are the transmission signal alone. In the images of the growth control (A, B and C), some auto-fluorescence was observed. Late trophozoites (normal arrow head) and haemozoin crystals, a digestion product of the malaria parasite (filled arrow head), were observed in image C. Images D, E and F, attributed to malaria-infected cells treated with conjugate 12, and images G, H and I, attributed to malaria-infected cells treated with conjugate 11, both had fluorescence in all erythrocytes. This indicated that there was no selectivity between infected and un-infected erythrocytes. However, conjugate fluorescence was present only within the erythrocytes; no fluorescence was present in the cell membranes or outside the erythrocytes. Presence of dead malaria parasites (stealth arrow head) was present in images F and I and a haemozoin crystal (filled arrow head) was present in image F, as a result of a deceased malaria parasite.

It is speculated that the conjugate was taken up into the erythrocytes, through the membrane. In addition, it is suggested that "vaccination" of the erythrocytes could be part of the mode of action, as the dormant/intact conjugate was present in all erythrocytes. The pH in erythrocytes is the same as blood pH, 7.4, and as a result conjugates would remain intact within the erythrocytes. Only when a merozoite entered and infected an erythrocyte would its food vacuole take up the conjugate, releasing the tyrothricin, and incapacitating the parasite. This is a possible mechanism explaining why no parasites with abnormal morphology or stunted growth, as well as no reinfection, were observed (as previously found for the tyrocidines).[10]

Microscopy

Blood smears were prepared at various incubation times for examination by light and fluorescence microscopy. Slides prepared for light microscopy were stained with Giemsa.

9. Conjugate Toxicity

Toxicity studies were conducted to assess whether the lower molecular mass PVP with conjugate Mr-2700 of the invention showed any toxicity towards human epithelial cells.

Cell Viability Assay:

Human umbilical vein endothelial cells (HUVECs) were seeded at a density of 80 000 cells per well in 48-well plates and maintained until 70-80% confluency was reached. The cell proliferation agent WST-1 (ab155902; Abcam, Cambridge, UK) was added to experimental wells, each well containing 1 ng/ml, 10 ng/ml or 1 μg/ml peptide-polymer conjugate, and were then incubated in a light-protected environment for 2 h. Viable cells have active mitochondrial dehydrogenases, which result in the production of formazan dye, measurable through spectrophotometry. Plates were placed on a shaker for 1 min to mix the well content, after which the absorbance was measured at 450 nm. Data are represented as a percentage of average control (Table 4).

TABLE 4

Summary of percentage cell viability of HUVEC cells challenged by the difference amounts of the antimalarial conjugate. Top values are % average viability ito the unchallenged control HUVEC cells and bottom value the standard deviation of 10 repeats.

| | Peptide amount | | |
|---|---|---|---|
| | 1 ng/ml | 10 ng/ml | 1 μg/ml |
| Repeat 1 | 110.5 | 119.5 | 153.0 |
| | 46.1 | 34.1 | 63.3 |
| Repeat 1 | 110.6 | 115.8 | 117.9 |
| | 44.2 | 20.4 | 20.6 |
| Repeat 1 | 111.2 | 112.6 | 125.6 |
| | 28.0 | 38.9 | 37.3 |

No statistically significant difference was observed between control and 1 ng/ml or 10 ng/ml concentrations of the conjugate in terms of the cell viability depending on the MTT reductive capacity. However, a small but statistically significant increase in reductive capacity was observed between the control and the 1 μg/ml treatment group (Table 4). This increased reductive capacity may either indicate greater mitochondrial respiration and function, which could serve as protective mechanism, or it may be a result of a stress response, where reductive capacity is increased as a coping mechanism.

Fluorescence Microscopy

Cells were stained with Hoechst 33342 and tetramethyl rhodamine ethylester (TMRE, 500 nM) by adding pre-warmed media with both dyes (1:200) to wells for 3 min, followed by fluorescence microscopy. At least three images were captured for each treatment group at 100× magnification using 360 nm, 492 and 572 nm excitation wavelengths. An F-view-II cooled CCD camera (Soft Imaging Systems, Olympus Corporation, Tokyo, Japan) mounted on a wide field inverted microscope (Olympus IX81, Olympus Corporation, Tokyo, Japan) with a Xenon-Arc burner (Olympus Biosystems GMBH, Hamburg, Germany) as a light source was used. Emission was collected with a UBG triple-bandpass emission filter cube (Chroma). Images were captured and processed using Olympus Cell^R (Hamburg, Germany) software.

Figure 20:
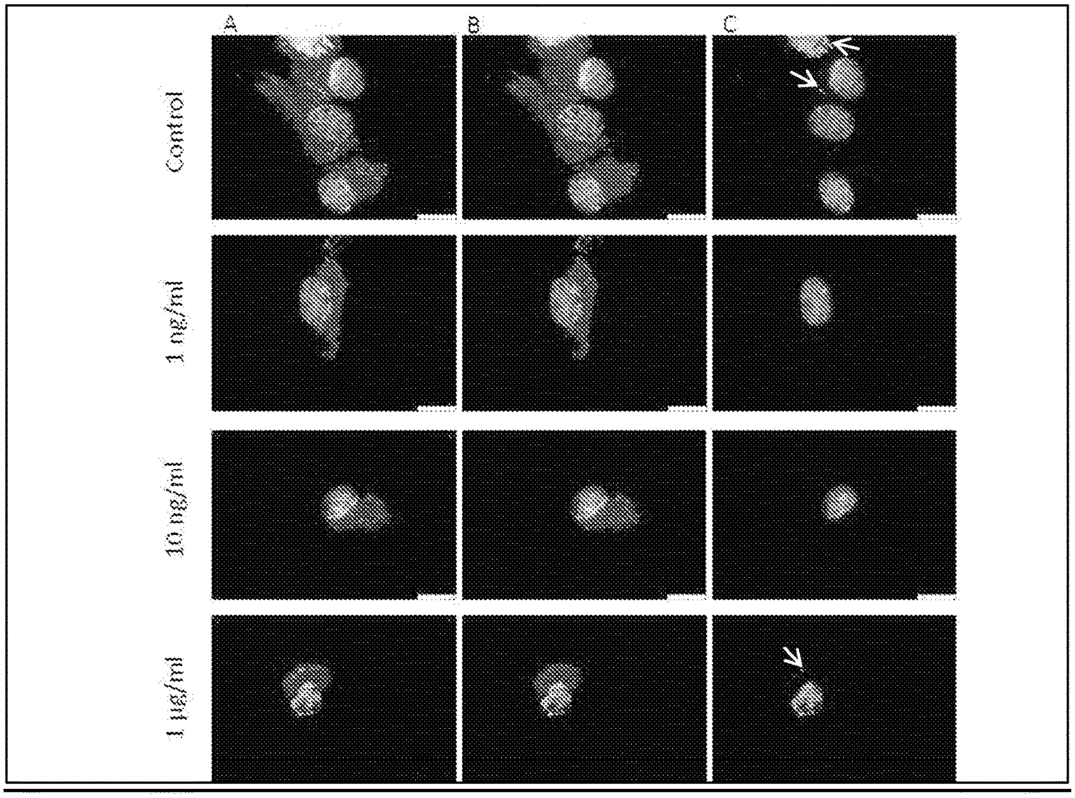
FIG. 20 shows HUVEC cells treated with different peptide-polymer conjugate concentrations. (A) nuclei (light grey), mitochondria (dark grey), and peptide-polymer conjugate (white, indicated with arrows), (B) nuclei and mitochondria, (C) nuclei and peptide-polymer conjugate. Scale bar=20 μm. No difference in mitochondrial network morphology is observed, no signs for fragmentation of fission as potential indicator of cellular stress. No nuclear condensation is observed.

The microscopy images showed that no nuclear condensation, as indicator for apoptotic cell death, is observed. The mitochondria display TMRE positive signal, and hence have a maintained polarisation, with a well-defined mitochondrial network morphology. The conjugate itself is rarely visible in the green channel, likely due to the very low fluorochrome concentration (FIG. 20). The conjugate therefore has no toxicity to human epithelial cells.

Statistical Analysis

One-way analysis of variance (ANOVA) with Bonferroni post hoc test was performed using Prism Graph Pad 5.0 to determine differences between groups. A p-value<0.05 was considered significant.

REFERENCES (1) Akeroyd, N.; Pfukwa, R.; Klumperman, B. Macromolecules 2009, 42, 3014.

(2) Goddard-Borger, E. D.; Stick, R. V. Org. Lett. 2007, 9, 3797.

(3) Hwang, J.; Li, R. C.; Maynard, H. D. J. Controlled Release 2007, 122, 279.

(4) Willcock, H.; O'Reilly, R. K. Polym. Chem. 2010, 1, 149.
(5) Canalle, L. A.; Lowik, D. W. P. M.; van Hest, J. C. M. Chem. Soc. Rev. 2010, 39, 329.
(6) EDA, K.; EDA, S.; SHERMAN, I. W. Am. J. Trop. Med. Hyg. 2004, 71, 190.
(7) Chan, J. W.; Yu, B.; Hoyle, C. E.; Lowe, A. B. Polymer 2009, 50, 3158.
(8) Oishi, M.; Nagasaki, Y.; Itaka, K.; Nishiyama, N.; Kataoka, K. J. Am. Chem. Soc. 2005, 127, 1624.
(9) Rautenbach, M.; Gerstner, G. D.; Vlok, N. M.; Kulenkampff, J.; Westerhoff, H. V. Anal. Biochem. 2006, 350, 81.
(10) Leussa, N.-N. A.,PhD thesis, Stellenbosch University, 2014.
(11) Vosloo J A, Stander M A, Leussa A N-N, SpatheIf B M, Rautenbach M. Microbiology. 2013, 159, 2200-2211, DOI: 10.1099/mic.0.068734-0.
(12) Oishi, M.; Sasaki, S.; Nagasaki, Y.; Kataoka, K. Biomacromolecules 2003, 4, 1426.

The invention claimed is:

1. A peptide-polymer conjugate comprising a polymer to which an antiplasmodial peptide is covalently attached, wherein the antiplasmodial peptide is a cyclic decapeptide having an amino acid sequence of cyclo($X^{10}$-$X^1$-Leu-D-Phe-Pro-$X^2$-$X^3$-$X^4$-$X^5$-$X^6$) (SEQ ID NO: 1), where:

$X^{10}$ is Val, Ile, or Leu;

$X^1$ is Orn or Lys;

$X^2$ is Val, Leu, Ile, Phe, Trp, or Tyr;

$X^3$ is the D-isomer of Val, Leu, Ile, Phe, Trp, Tyr, or L-isomer of Orn or Lys;

$X^4$ is Asn, Gln or Leu;

$X^5$ is Gln or the D-isomer of Phe; and $X^6$ is Tyr, Phe, Trp, Pro, or hydroxyproline;

wherein the antiplasmodial peptide is conjugated to the polymer by way of a linkage comprising a beta-thiopropionate or beta-thiopropionamide, which causes the ester or amide linkage to be unstable and to release the antiplasmodial peptide at acidic pH, the linkage being formed by:

modifying the antiplasmodial peptide to comprise an acrylate ester or acrylamide, and covalently linking the acrylate ester or acrylamide of the modified antiplasmodial peptide to a thiol end-group of a chain end of the polymer via Michael addition, and wherein the peptide-polymer conjugate can be taken up by erythrocytes and has activity against a malaria parasite.

2. The peptide-polymer conjugate according to claim 1, wherein the cyclic decapeptide is a tyrocidine with the sequence cyclo($X^{10}$-$X^1$-Leu-D-Phe-Pro-$X^7$-$X^8$-Asn-Gln-$X^9$) (SEQ ID NO: 2), where:

$X^{10}$ is Val, Ile, or Leu;

$X^1$ is Orn or Lys;

$X^7$ is Trp or Phe;

$X^8$ is D-Trp or D-Phe; and $X^9$ is Tyr, Trp, or Phe.

3. The peptide-polymer conjugate according to claim 1, wherein the cyclic decapeptide is gramicidin S, with the amino acid sequence of cyclo(Val-$X^1$-Leu-D-Phe-Pro-Val-$X^1$-Leu-D-Phe-Pro) (SEQ ID NO: 3).

4. The peptide-polymer conjugate according to claim 1, wherein the cyclic decapeptide has an amino acid sequence selected from any one of SEQ ID NOs: 6-177.

5. The peptide-polymer conjugate according to claim 1, wherein the polymer is selected from the group consisting of poly(N-vinylpyrrolidone), poly(ethylene oxide), poly((ethylene oxide)-co-(propylene oxide)), poly(oligo(ethylene oxide)acrylate), poly(2-hydroxypropyl acrylamide), and poly(oligo(ethylene oxide)methacrylate).

6. The peptide-polymer conjugate according to claim 1, wherein the antiplasmodial peptide is conjugated to the chain end of the polymer.

7. The peptide-polymer conjugate according to claim 1, further comprising a hydrophilic targeting ligand selected from the group consisting of peptides having amino acid sequences of SEQ ID NOs: 178 185.

8. A method of treating malaria, the method comprising administering a therapeutically effective amount of a peptide-polymer conjugate as claimed in claim 1 to a patient in need thereof.

9. The method according to claim 8, wherein the therapeutically effective amount of the peptide-polymer conjugate comprises an amount of the peptide which is sub-therapeutic for treating malaria when the peptide is administered in an unconjugated form.

* * * * *

SEQUENCE LISTING

```
<160> NUMBER OF SEQ ID NOS: 185

<210> SEQ ID NO 1
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: VARIANT
<222> LOCATION: (1)..(1)
<223> OTHER INFORMATION: X10 = V, L, or I
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (6)..(6)
<223> OTHER INFORMATION: X2 = V, L, I, F, W or Y
<220> FEATURE:
<221> NAME/KEY: VARIANT
<222> LOCATION: (7)..(7)
<223> OTHER INFORMATION: X3 = v, l, i, f, w, y, O or K
<220> FEATURE:
<221> NAME/KEY: VARIANT
<222> LOCATION: (8)..(8)
<223> OTHER INFORMATION: X4 = N, Q or L
<220> FEATURE:
<221> NAME/KEY: VARIANT
<222> LOCATION: (9)..(9)
<223> OTHER INFORMATION: X5 = Q or f
<220> FEATURE:
<221> NAME/KEY: VARIANT
<222> LOCATION: (10)..(10)
<223> OTHER INFORMATION: X6 = Y, F, W, P or H

<400> SEQUENCE: 1

Xaa Xaa Leu Phe Pro Xaa Xaa Xaa Xaa Xaa
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: VARIANT
<222> LOCATION: (1)..(1)
<223> OTHER INFORMATION: X10 = V, L, or I
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (6)..(6)
<223> OTHER INFORMATION: X7 = W or F
<220> FEATURE:
<221> NAME/KEY: VARIANT
<222> LOCATION: (7)..(7)
<223> OTHER INFORMATION: X8 = w or f
```

<220> FEATURE:
<221> NAME/KEY: VARIANT
<222> LOCATION: (10)..(10)
<223> OTHER INFORMATION: X9 = Y, W, or F

<400> SEQUENCE: 2

Xaa Xaa Leu Phe Pro Xaa Xaa Asn Gln Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (7)..(7)
<223> OTHER INFORMATION: X1 = O or K

<400> SEQUENCE: 3

Val Xaa Leu Phe Pro Val Xaa Leu Phe Pro
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 4

Val Xaa Leu Phe Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Artificial construct; Cyclic polypeptide

<400> SEQUENCE: 5

Phe Phe Asn Gln Tyr
1               5

<210> SEQ ID NO 6
<211> LENGTH: 10
<212> TYPE: PRT
<213> ORGANISM: Bacillus aneurinolyticus

<400> SEQUENCE: 6

Val Lys Leu Phe Pro Trp Trp Asn Gln Tyr
1               5                   10

<210> SEQ ID NO 7
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 7

Val Xaa Leu Phe Pro Trp Trp Asn Gln Tyr
1 5 10

<210> SEQ ID NO 8
<211> LENGTH: 10
<212> TYPE: PRT
<213> ORGANISM: Bacillus aneurinolyticus

<400> SEQUENCE: 8

Val Lys Leu Phe Pro Trp Phe Asn Gln Tyr
1 5 10

<210> SEQ ID NO 9
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 9

Val Xaa Leu Phe Pro Trp Phe Asn Gln Tyr
1 5 10

<210> SEQ ID NO 10
<211> LENGTH: 10
<212> TYPE: PRT
<213> ORGANISM: Bacillus aneurinolyticus

<400> SEQUENCE: 10

Val Lys Leu Phe Pro Phe Trp Asn Gln Tyr
1 5 10

<210> SEQ ID NO 11
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 11

Val Xaa Leu Phe Pro Phe Trp Asn Gln Tyr
1 5 10

<210> SEQ ID NO 12
<211> LENGTH: 10
<212> TYPE: PRT
<213> ORGANISM: Bacillus aneurinolyticus

<400> SEQUENCE: 12

Val Lys Leu Phe Pro Phe Phe Asn Gln Tyr
1 5 10

<210> SEQ ID NO 13
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)

```
<223> OTHER INFORMATION: Orn

<400> SEQUENCE: 13

Val Xaa Leu Phe Pro Phe Phe Asn Gln Tyr
1               5                   10


<210> SEQ ID NO 14
<211> LENGTH: 10
<212> TYPE: PRT
<213> ORGANISM: Bacillus aneurinolyticus

<400> SEQUENCE: 14

Val Lys Leu Phe Pro Tyr Trp Asn Gln Tyr
1               5                   10


<210> SEQ ID NO 15
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 15

Val Xaa Leu Phe Pro Tyr Trp Asn Gln Tyr
1               5                   10


<210> SEQ ID NO 16
<211> LENGTH: 10
<212> TYPE: PRT
<213> ORGANISM: Bacillus aneurinolyticus

<400> SEQUENCE: 16

Val Lys Leu Phe Pro Tyr Phe Asn Gln Tyr
1               5                   10


<210> SEQ ID NO 17
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 17

Val Xaa Leu Phe Pro Tyr Phe Asn Gln Tyr
1               5                   10


<210> SEQ ID NO 18
<211> LENGTH: 10
<212> TYPE: PRT
<213> ORGANISM: Bacillus aneurinolyticus

<400> SEQUENCE: 18

Val Lys Leu Phe Pro Phe Tyr Asn Gln Tyr
1               5                   10


<210> SEQ ID NO 19
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn
```

<400> SEQUENCE: 19

Val Xaa Leu Phe Pro Phe Tyr Asn Gln Tyr
1 5 10

<210> SEQ ID NO 20
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 20

Val Lys Leu Phe Pro Trp Tyr Asn Gln Tyr
1 5 10

<210> SEQ ID NO 21
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 21

Val Xaa Leu Phe Pro Trp Tyr Asn Gln Tyr
1 5 10

<210> SEQ ID NO 22
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 22

Leu Lys Leu Phe Pro Trp Trp Asn Gln Tyr
1 5 10

<210> SEQ ID NO 23
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 23

Leu Xaa Leu Phe Pro Trp Trp Asn Gln Tyr
1 5 10

<210> SEQ ID NO 24
<211> LENGTH: 10
<212> TYPE: PRT
<213> ORGANISM: Bacillus aneurinolyticus

<400> SEQUENCE: 24

Leu Lys Leu Phe Pro Trp Phe Asn Gln Tyr
1 5 10

<210> SEQ ID NO 25

<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 25

```
Leu Xaa Leu Phe Pro Trp Phe Asn Gln Tyr
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 26

```
Leu Lys Leu Phe Pro Phe Trp Asn Gln Tyr
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 27

```
Leu Xaa Leu Phe Pro Phe Trp Asn Gln Tyr
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 28

```
Leu Lys Leu Phe Pro Phe Phe Asn Gln Tyr
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 29

```
Leu Xaa Leu Phe Pro Phe Phe Asn Gln Tyr
1               5                   10
```

<210> SEQ ID NO 30
<211> LENGTH: 10
<212> TYPE: PRT
<213> ORGANISM: Artificial Sequence
<220> FEATURE:

<223> OTHER INFORMATION: Artificial construct; Cyclic polypeptide

<400> SEQUENCE: 30

Leu Lys Leu Phe Pro Tyr Trp Asn Gln Tyr
1 5 10

<210> SEQ ID NO 31
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 31

Leu Xaa Leu Phe Pro Tyr Trp Asn Gln Tyr
1 5 10

<210> SEQ ID NO 32
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 32

Leu Lys Leu Phe Pro Tyr Phe Asn Gln Tyr
1 5 10

<210> SEQ ID NO 33
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 33

Leu Xaa Leu Phe Pro Tyr Phe Asn Gln Tyr
1 5 10

<210> SEQ ID NO 34
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 34

Leu Lys Leu Phe Pro Phe Tyr Asn Gln Tyr
1 5 10

<210> SEQ ID NO 35
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 35

Leu Xaa Leu Phe Pro Phe Tyr Asn Gln Tyr
1 5 10

<210> SEQ ID NO 36
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 36

Leu Lys Leu Phe Pro Trp Tyr Asn Gln Tyr
1 5 10

<210> SEQ ID NO 37
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 37

Leu Xaa Leu Phe Pro Trp Tyr Asn Gln Tyr
1 5 10

<210> SEQ ID NO 38
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 38

Ile Lys Leu Phe Pro Trp Trp Asn Gln Tyr
1 5 10

<210> SEQ ID NO 39
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 39

Ile Xaa Leu Phe Pro Trp Trp Asn Gln Tyr
1 5 10

<210> SEQ ID NO 40
<211> LENGTH: 10
<212> TYPE: PRT
<213> ORGANISM: Bacillus aneurinolyticus

<400> SEQUENCE: 40

Ile Lys Leu Phe Pro Trp Phe Asn Gln Tyr
1 5 10

<210> SEQ ID NO 41
<211> LENGTH: 10

-continued

<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 41

Ile Xaa Leu Phe Pro Trp Phe Asn Gln Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 42

Ile Lys Leu Phe Pro Phe Trp Asn Gln Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 43

Ile Xaa Leu Phe Pro Phe Trp Asn Gln Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 44

Ile Lys Leu Phe Pro Phe Phe Asn Gln Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 45

Ile Xaa Leu Phe Pro Phe Phe Asn Gln Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 46

Ile Lys Leu Phe Pro Tyr Trp Asn Gln Tyr
1 5 10

<210> SEQ ID NO 47
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 47

Ile Xaa Leu Phe Pro Tyr Trp Asn Gln Tyr
1 5 10

<210> SEQ ID NO 48
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 48

Ile Lys Leu Phe Pro Tyr Phe Asn Gln Tyr
1 5 10

<210> SEQ ID NO 49
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 49

Ile Xaa Leu Phe Pro Tyr Phe Asn Gln Tyr
1 5 10

<210> SEQ ID NO 50
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 50

Ile Lys Leu Phe Pro Phe Tyr Asn Gln Tyr
1 5 10

<210> SEQ ID NO 51
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 51

```
Ile Xaa Leu Phe Pro Phe Tyr Asn Gln Tyr
1               5                   10


<210> SEQ ID NO 52
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 52

Ile Lys Leu Phe Pro Trp Tyr Asn Gln Tyr
1               5                   10


<210> SEQ ID NO 53
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 53

Ile Xaa Leu Phe Pro Trp Tyr Asn Gln Tyr
1               5                   10


<210> SEQ ID NO 54
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 54

Val Lys Leu Phe Pro Leu Trp Asn Gln Tyr
1               5                   10


<210> SEQ ID NO 55
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 55

Val Xaa Leu Phe Pro Leu Trp Asn Gln Tyr
1               5                   10


<210> SEQ ID NO 56
<211> LENGTH: 10
<212> TYPE: PRT
<213> ORGANISM: Bacillus aneurinolyticus

<400> SEQUENCE: 56

Val Lys Leu Phe Pro Leu Phe Asn Gln Tyr
1               5                   10


<210> SEQ ID NO 57
<211> LENGTH: 10
<212> TYPE: PRT
```

<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 57

Val Xaa Leu Phe Pro Leu Phe Asn Gln Tyr
1 5 10

<210> SEQ ID NO 58
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 58

Val Lys Leu Phe Pro Leu Tyr Asn Gln Tyr
1 5 10

<210> SEQ ID NO 59
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 59

Val Xaa Leu Phe Pro Leu Tyr Asn Gln Tyr
1 5 10

<210> SEQ ID NO 60
<211> LENGTH: 10
<212> TYPE: PRT
<213> ORGANISM: Bacillus aneurinolyticus

<400> SEQUENCE: 60

Val Lys Leu Phe Pro Trp Trp Asn Gln Trp
1 5 10

<210> SEQ ID NO 61
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 61

Val Xaa Leu Phe Pro Trp Trp Asn Gln Trp
1 5 10

<210> SEQ ID NO 62
<211> LENGTH: 10
<212> TYPE: PRT
<213> ORGANISM: Bacillus aneurinolyticus

<400> SEQUENCE: 62

Val Lys Leu Phe Pro Trp Phe Asn Gln Trp
1 5 10

<210> SEQ ID NO 63
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 63

Val Xaa Leu Phe Pro Trp Phe Asn Gln Trp
1 5 10

<210> SEQ ID NO 64
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 64

Val Lys Leu Phe Pro Phe Trp Asn Gln Trp
1 5 10

<210> SEQ ID NO 65
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 65

Val Xaa Leu Phe Pro Phe Trp Asn Gln Trp
1 5 10

<210> SEQ ID NO 66
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 66

Val Lys Leu Phe Pro Phe Phe Asn Gln Trp
1 5 10

<210> SEQ ID NO 67
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 67

Val Xaa Leu Phe Pro Phe Phe Asn Gln Trp
1 5 10

<210> SEQ ID NO 68
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 68

Val Lys Leu Phe Pro Tyr Trp Asn Gln Trp
1 5 10

<210> SEQ ID NO 69
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 69

Val Xaa Leu Phe Pro Tyr Trp Asn Gln Trp
1 5 10

<210> SEQ ID NO 70
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 70

Val Lys Leu Phe Pro Tyr Phe Asn Gln Trp
1 5 10

<210> SEQ ID NO 71
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 71

Val Xaa Leu Phe Pro Tyr Phe Asn Gln Trp
1 5 10

<210> SEQ ID NO 72
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 72

Val Lys Leu Phe Pro Phe Tyr Asn Gln Trp
1 5 10

<210> SEQ ID NO 73
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 73

Val Xaa Leu Phe Pro Phe Tyr Asn Gln Trp
1 5 10

<210> SEQ ID NO 74
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 74

Val Lys Leu Phe Pro Trp Tyr Asn Gln Trp
1 5 10

<210> SEQ ID NO 75
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 75

Val Xaa Leu Phe Pro Trp Tyr Asn Gln Trp
1 5 10

<210> SEQ ID NO 76
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 76

Leu Lys Leu Phe Pro Trp Trp Asn Gln Trp
1 5 10

<210> SEQ ID NO 77
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 77

Leu Xaa Leu Phe Pro Trp Trp Asn Gln Trp
1 5 10

<210> SEQ ID NO 78
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 78

Leu Lys Leu Phe Pro Trp Phe Asn Gln Trp
1 5 10

<210> SEQ ID NO 79

<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 79

Leu Xaa Leu Phe Pro Trp Phe Asn Gln Trp
1 5 10

<210> SEQ ID NO 80
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 80

Leu Lys Leu Phe Pro Phe Trp Asn Gln Trp
1 5 10

<210> SEQ ID NO 81
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 81

Leu Xaa Leu Phe Pro Phe Trp Asn Gln Trp
1 5 10

<210> SEQ ID NO 82
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 82

Leu Lys Leu Phe Pro Phe Phe Asn Gln Trp
1 5 10

<210> SEQ ID NO 83
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 83

Leu Xaa Leu Phe Pro Phe Phe Asn Gln Trp
1 5 10

<210> SEQ ID NO 84
<211> LENGTH: 10
<212> TYPE: PRT

<213> ORGANISM: Artificial Sequence
<220> FEATURE:
<223> OTHER INFORMATION: Artificial construct; Cyclic polypeptide

<400> SEQUENCE: 84

Leu Lys Leu Phe Pro Tyr Trp Asn Gln Trp
1 5 10

<210> SEQ ID NO 85
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 85

Leu Xaa Leu Phe Pro Tyr Trp Asn Gln Trp
1 5 10

<210> SEQ ID NO 86
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 86

Leu Lys Leu Phe Pro Tyr Phe Asn Gln Trp
1 5 10

<210> SEQ ID NO 87
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 87

Leu Xaa Leu Phe Pro Tyr Phe Asn Gln Trp
1 5 10

<210> SEQ ID NO 88
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 88

Leu Lys Leu Phe Pro Phe Tyr Asn Gln Trp
1 5 10

<210> SEQ ID NO 89
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)

<223> OTHER INFORMATION: Orn

<400> SEQUENCE: 89

Leu Xaa Leu Phe Pro Phe Tyr Asn Gln Trp
1 5 10

<210> SEQ ID NO 90
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 90

Leu Lys Leu Phe Pro Trp Tyr Asn Gln Trp
1 5 10

<210> SEQ ID NO 91
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 91

Leu Xaa Leu Phe Pro Trp Tyr Asn Gln Trp
1 5 10

<210> SEQ ID NO 92
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 92

Ile Lys Leu Phe Pro Trp Trp Asn Gln Trp
1 5 10

<210> SEQ ID NO 93
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 93

Ile Xaa Leu Phe Pro Trp Trp Asn Gln Trp
1 5 10

<210> SEQ ID NO 94
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 94

Ile Lys Leu Phe Pro Trp Phe Asn Gln Trp
1 5 10

<210> SEQ ID NO 95
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 95

Ile Xaa Leu Phe Pro Trp Phe Asn Gln Trp
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 96

Ile Lys Leu Phe Pro Phe Trp Asn Gln Trp
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 97

Ile Xaa Leu Phe Pro Phe Trp Asn Gln Trp
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 98

Ile Lys Leu Phe Pro Phe Phe Asn Gln Trp
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 99

Ile Xaa Leu Phe Pro Phe Phe Asn Gln Trp
1               5                   10

-continued

<210> SEQ ID NO 100
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 100

Ile Lys Leu Phe Pro Tyr Trp Asn Gln Trp
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 101

Ile Xaa Leu Phe Pro Tyr Trp Asn Gln Trp
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 102

Ile Lys Leu Phe Pro Tyr Phe Asn Gln Trp
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 103

Ile Xaa Leu Phe Pro Tyr Phe Asn Gln Trp
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 104

Ile Lys Leu Phe Pro Phe Tyr Asn Gln Trp
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 105

Ile Xaa Leu Phe Pro Phe Tyr Asn Gln Trp
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 106

Ile Lys Leu Phe Pro Trp Tyr Asn Gln Trp
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 107

Ile Xaa Leu Phe Pro Trp Tyr Asn Gln Trp
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 108

Val Lys Leu Phe Pro Leu Trp Asn Gln Trp
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 109

Val Xaa Leu Phe Pro Leu Trp Asn Gln Trp
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 110

-continued

Val Lys Leu Phe Pro Leu Phe Asn Gln Trp
1 5 10

<210> SEQ ID NO 111
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 111

Val Xaa Leu Phe Pro Leu Phe Asn Gln Trp
1 5 10

<210> SEQ ID NO 112
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 112

Val Lys Leu Phe Pro Leu Tyr Asn Gln Trp
1 5 10

<210> SEQ ID NO 113
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 113

Val Xaa Leu Phe Pro Leu Tyr Asn Gln Trp
1 5 10

<210> SEQ ID NO 114
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 114

Val Lys Leu Phe Pro Trp Trp Asn Gln Phe
1 5 10

<210> SEQ ID NO 115
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 115

Val Xaa Leu Phe Pro Trp Trp Asn Gln Phe 1 5 10

<210> SEQ ID NO 116
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 116

Val Lys Leu Phe Pro Trp Phe Asn Gln Phe
1 5 10

<210> SEQ ID NO 117
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 117

Val Xaa Leu Phe Pro Trp Phe Asn Gln Phe
1 5 10

<210> SEQ ID NO 118
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 118

Val Lys Leu Phe Pro Phe Trp Asn Gln Phe
1 5 10

<210> SEQ ID NO 119
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 119

Val Xaa Leu Phe Pro Phe Trp Asn Gln Phe
1 5 10

<210> SEQ ID NO 120
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 120

Val Lys Leu Phe Pro Phe Phe Asn Gln Phe
1 5 10

<210> SEQ ID NO 121
<211> LENGTH: 10
<212> TYPE: PRT
<213> ORGANISM: Bacillus aneurinolyticus
<220> FEATURE:

<221> NAME/KEY: MOD_RES
<222> LOCATION: (2)..(2)
<223> OTHER INFORMATION: Orn

<400> SEQUENCE: 121

Val Xaa Leu Phe Pro Phe Phe Asn Gln Phe
1 5 10

<210> SEQ ID NO 122
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 122

Val Lys Leu Phe Pro Tyr Trp Asn Gln Phe
1 5 10

<210> SEQ ID NO 123
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 123

Val Xaa Leu Phe Pro Tyr Trp Asn Gln Phe
1 5 10

<210> SEQ ID NO 124
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 124

Val Lys Leu Phe Pro Tyr Phe Asn Gln Phe
1 5 10

<210> SEQ ID NO 125
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 125

Val Xaa Leu Phe Pro Tyr Phe Asn Gln Phe
1 5 10

<210> SEQ ID NO 126
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 126

Val Lys Leu Phe Pro Phe Tyr Asn Gln Phe
1 5 10

<210> SEQ ID NO 127
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 127

Val Xaa Leu Phe Pro Phe Tyr Asn Gln Phe
1 5 10

<210> SEQ ID NO 128
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 128

Val Lys Leu Phe Pro Trp Tyr Asn Gln Phe
1 5 10

<210> SEQ ID NO 129
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 129

Val Xaa Leu Phe Pro Trp Tyr Asn Gln Phe
1 5 10

<210> SEQ ID NO 130
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 130

Leu Lys Leu Phe Pro Trp Trp Asn Gln Phe
1 5 10

<210> SEQ ID NO 131
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 131

Leu Xaa Leu Phe Pro Trp Trp Asn Gln Phe
1 5 10

<210> SEQ ID NO 132
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 132

Leu Lys Leu Phe Pro Trp Phe Asn Gln Phe
1 5 10

<210> SEQ ID NO 133
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 133

Leu Xaa Leu Phe Pro Trp Phe Asn Gln Phe
1 5 10

<210> SEQ ID NO 134
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 134

Leu Lys Leu Phe Pro Phe Trp Asn Gln Phe
1 5 10

<210> SEQ ID NO 135
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 135

Leu Xaa Leu Phe Pro Phe Trp Asn Gln Phe
1 5 10

<210> SEQ ID NO 136
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 136

Leu Lys Leu Phe Pro Tyr Trp Asn Gln Phe
1 5 10

<210> SEQ ID NO 137
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 137

Leu Xaa Leu Phe Pro Tyr Trp Asn Gln Phe
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 138

Leu Lys Leu Phe Pro Tyr Phe Asn Gln Phe
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 139

Leu Xaa Leu Phe Pro Tyr Phe Asn Gln Phe
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 140

Leu Lys Leu Phe Pro Phe Tyr Asn Gln Phe
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 141

Leu Xaa Leu Phe Pro Phe Tyr Asn Gln Phe
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 142

Leu Lys Leu Phe Pro Trp Tyr Asn Gln Phe
1 5 10

<210> SEQ ID NO 143
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 143

Leu Xaa Leu Phe Pro Trp Tyr Asn Gln Phe
1 5 10

<210> SEQ ID NO 144
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 144

Leu Lys Leu Phe Pro Phe Phe Asn Gln Phe
1 5 10

<210> SEQ ID NO 145
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 145

Leu Xaa Leu Phe Pro Phe Phe Asn Gln Phe
1 5 10

<210> SEQ ID NO 146
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 146

Ile Lys Leu Phe Pro Trp Trp Asn Gln Phe
1 5 10

<210> SEQ ID NO 147
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 147

Ile Xaa Leu Phe Pro Trp Trp Asn Gln Phe
1 5 10

<210> SEQ ID NO 148
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 148

Ile Lys Leu Phe Pro Trp Phe Asn Gln Phe
1 5 10

<210> SEQ ID NO 149
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 149

Ile Xaa Leu Phe Pro Trp Phe Asn Gln Phe
1 5 10

<210> SEQ ID NO 150
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 150

Ile Lys Leu Phe Pro Phe Trp Asn Gln Phe
1 5 10

<210> SEQ ID NO 151
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 151

Ile Xaa Leu Phe Pro Phe Trp Asn Gln Phe
1 5 10

<210> SEQ ID NO 152
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 152

Ile Lys Leu Phe Pro Tyr Trp Asn Gln Phe
1 5 10

<210> SEQ ID NO 153

```
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 153

Ile Xaa Leu Phe Pro Tyr Trp Asn Gln Phe
1               5                   10


<210> SEQ ID NO 154
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 154

Ile Lys Leu Phe Pro Tyr Phe Asn Gln Phe
1               5                   10


<210> SEQ ID NO 155
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 155

Ile Xaa Leu Phe Pro Tyr Phe Asn Gln Phe
1               5                   10


<210> SEQ ID NO 156
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 156

Ile Lys Leu Phe Pro Phe Tyr Asn Gln Phe
1               5                   10


<210> SEQ ID NO 157
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 157

Ile Xaa Leu Phe Pro Phe Tyr Asn Gln Phe
1               5                   10


<210> SEQ ID NO 158
<211> LENGTH: 10
<212> TYPE: PRT
```

<213> ORGANISM: Artificial Sequence
<220> FEATURE:
<223> OTHER INFORMATION: Artificial construct; Cyclic polypeptide

<400> SEQUENCE: 158

Ile Lys Leu Phe Pro Trp Tyr Asn Gln Phe
1 5 10

<210> SEQ ID NO 159
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 159

Ile Xaa Leu Phe Pro Trp Tyr Asn Gln Phe
1 5 10

<210> SEQ ID NO 160
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 160

Ile Lys Leu Phe Pro Phe Phe Asn Gln Phe
1 5 10

<210> SEQ ID NO 161
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 161

Ile Xaa Leu Phe Pro Phe Phe Asn Gln Phe
1 5 10

<210> SEQ ID NO 162
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 162

Val Lys Leu Phe Pro Leu Trp Asn Gln Phe
1 5 10

<210> SEQ ID NO 163
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)

<223> OTHER INFORMATION: Orn

<400> SEQUENCE: 163

Val Xaa Leu Phe Pro Leu Trp Asn Gln Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 164

Val Lys Leu Phe Pro Leu Phe Asn Gln Phe
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 165

Val Xaa Leu Phe Pro Leu Phe Asn Gln Phe
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 166

Val Lys Leu Phe Pro Leu Tyr Asn Gln Phe
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 167

Val Xaa Leu Phe Pro Leu Tyr Asn Gln Phe
1               5                   10

<210> SEQ ID NO 168
<211> LENGTH: 10
<212> TYPE: PRT
<213> ORGANISM: Aneurinibacillus migulanus
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)

<223> OTHER INFORMATION: Orn

<400> SEQUENCE: 168

Val Xaa Leu Phe Pro Val Xaa Leu Phe Pro
1 5 10

<210> SEQ ID NO 169
<211> LENGTH: 10
<212> TYPE: PRT
<213> ORGANISM: Aneurinibacillus migulanus
<220> FEATURE:
<221> NAME/KEY: MOD_RES
<222> LOCATION: (7)..(7)
<223> OTHER INFORMATION: Orn

<400> SEQUENCE: 169

Val Lys Leu Phe Pro Val Xaa Leu Phe Pro
1 5 10

<210> SEQ ID NO 170
<211> LENGTH: 10
<212> TYPE: PRT
<213> ORGANISM: Aneurinibacillus migulanus

<400> SEQUENCE: 170

Val Lys Leu Phe Pro Val Lys Leu Phe Pro
1 5 10

<210> SEQ ID NO 171
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 171

Leu Xaa Leu Phe Pro Val Xaa Leu Phe Pro
1 5 10

<210> SEQ ID NO 172
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (7)..(7)
<223> OTHER INFORMATION: Orn

<400> SEQUENCE: 172

Leu Lys Leu Phe Pro Val Xaa Leu Phe Pro
1 5 10

<210> SEQ ID NO 173
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:

<221> NAME/KEY: MOD_RES
<222> LOCATION: (2)..(2)
<223> OTHER INFORMATION: Orn

<400> SEQUENCE: 173

Leu Xaa Leu Phe Pro Val Lys Leu Phe Pro
1 5 10

<210> SEQ ID NO 174
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 174

Leu Lys Leu Phe Pro Val Lys Leu Phe Pro
1 5 10

<210> SEQ ID NO 175
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 175

Leu Xaa Leu Phe Pro Leu Xaa Leu Phe Pro
1 5 10

<210> SEQ ID NO 176
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (7)..(7)
<223> OTHER INFORMATION: Orn

<400> SEQUENCE: 176

Leu Lys Leu Phe Pro Leu Xaa Leu Phe Pro
1 5 10

<210> SEQ ID NO 177
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 177

Leu Lys Leu Phe Pro Leu Lys Leu Phe Pro
1 5 10

<210> SEQ ID NO 178
<211> LENGTH: 7
<212> TYPE: PRT
<213> ORGANISM: Artificial Sequence
<220> FEATURE:

<223> OTHER INFORMATION: Synthetic sequence which targets en epitope on red blood cells infected with malaria parasite

<400> SEQUENCE: 178

Gly Ser Arg Ser Lys Gly Thr
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic sequence which targets en epitope on red blood cells infected with malaria parasite

<400> SEQUENCE: 179

Leu Val Asp Ala Ala Ala Leu
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic sequence which targets en epitope on red blood cells infected with malaria parasite

<400> SEQUENCE: 180

Pro Ile Ala Leu Gly Leu Lys
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic sequence which targets en epitope on red blood cells infected with malaria parasite

<400> SEQUENCE: 181

Gly Gly Pro Leu Lys Gly Leu
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic sequence which targets en epitope on red blood cells infected with malaria parasite

<400> SEQUENCE: 182

Ile Asn Leu Gly Leu Thr Met
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic sequence which targets en epitope on red blood cells infected with malaria parasite

<400> SEQUENCE: 183

Phe Ser Leu Gly Leu Ile Lys
1               5

-continued

```
<210> SEQ ID NO 184
<211> LENGTH: 7
<212> TYPE: PRT
<213> ORGANISM: Artificial Sequence
<220> FEATURE:
<223> OTHER INFORMATION: Synthetic sequence which targets en epitope on
      red blood cells infected with malaria parasite

<400> SEQUENCE: 184

Pro Ala Tyr Lys Leu Tyr Ser
1               5


<210> SEQ ID NO 185
<211> LENGTH: 7
<212> TYPE: PRT
<213> ORGANISM: Artificial Sequence
<220> FEATURE:
<223> OTHER INFORMATION: Synthetic sequence which targets en epitope on
      red blood cells infected with malaria parasite

<400> SEQUENCE: 185

Asn Ser Val Gly Gly Arg Ser
1               5
```